US008690569B2

(12) United States Patent
Machado et al.

(10) Patent No.: US 8,690,569 B2
(45) Date of Patent: Apr. 8, 2014

(54) GUIDE TUBE POSITIONING METHOD IN POLYMERIC MATERIAL PLATE, TOMOGRAPHIC REFERENCE SUPPORT AND GUIDE TUBE POSITIONING DEVICE

(76) Inventors: Asbel Rodrigues Machado, Uberlandia-MG (BR); Eder Ferreira Rangel, Uberlandia-MG (BR); Keuler Ferreira Rangel, Uberlandia-MG (BR)

( * ) Notice: Subject to any disclaimer, the term of this patent is extended or adjusted under 35 U.S.C. 154(b) by 0 days.

(21) Appl. No.: 13/445,464

(22) Filed: Apr. 12, 2012

(65) Prior Publication Data

US 2012/0283737 A1    Nov. 8, 2012

Related U.S. Application Data

(63) Continuation-in-part of application No. 12/248,377, filed on Oct. 9, 2008, now abandoned.

(51) Int. Cl.
    *A61C 19/04*    (2006.01)
(52) U.S. Cl.
    USPC .............................................. 433/72; 433/75
(58) Field of Classification Search
    USPC .................... 433/72–76, 49–50, 53–68, 229;
                         33/511–514; 606/96
    See application file for complete search history.

(56) References Cited

U.S. PATENT DOCUMENTS

| 2,376,384 A | 5/1945 | Ringle et al. |
| 2,412,594 A | 12/1946 | Antonidis |
| 2,491,635 A | 12/1949 | Allen, Jr. |
| 2,552,463 A | 5/1951 | Searles |
| 2,669,889 A | 2/1954 | Huller |
| 2,703,453 A | 3/1955 | Landis |
| 2,724,899 A | 11/1955 | Stoll et al. |
| 3,627,904 A | 12/1971 | Milne |
| 3,637,272 A | 1/1972 | Christiansen |
| 3,874,808 A | 4/1975 | Zaccardelli et al. |
| 4,213,658 A | 7/1980 | Shaw |
| 4,570,952 A | 2/1986 | Heimbigner et al. |
| 5,015,183 A | 5/1991 | Fenick |
| 5,222,892 A * | 6/1993 | Perry .............................. 433/75 |
| 5,551,873 A | 9/1996 | Aiba |
| 5,556,278 A | 9/1996 | Meitner |
| 5,599,183 A | 2/1997 | Razdolsky et al. |
| 5,993,208 A | 11/1999 | Jonjic |
| 6,186,781 B1 | 2/2001 | Iba |
| 6,250,919 B1 | 6/2001 | Haje |
| 6,634,883 B2 | 10/2003 | Ranalli |

(Continued)

OTHER PUBLICATIONS american-1, Combination Chip Breaker and Directed Coolant Bushing, All American Products Co., captured Mar. 31, 2006.

(Continued)

*Primary Examiner* — Cris L Rodriguez
*Assistant Examiner* — Edward Moran
(74) *Attorney, Agent, or Firm* — Alston & Bird LLP

(57) ABSTRACT

A method is described for positioning a guide tube on a plate to be positioned over a patient's mandible or maxilla, forming a surgical guide that allows for positioning the guide tube on the exact position so as to enable the drilling of a perfect hole in the patient's bone portion and the subsequent positioning of an implant exactly on the planned spot. A tomographic reference support is described for fixing a guide tube positioning device, and a guide tube positioning device is described for positioning one or more guide tubes on an acrylic plate or the like, configuring a surgical guide.

6 Claims, 17 Drawing Sheets

(56) References Cited

U.S. PATENT DOCUMENTS

| | | |
|---|---|---|
| 7,014,461 B2 | 3/2006 | Weinstein |
| 7,086,860 B2 | 8/2006 | Schuman et al. |
| 7,097,451 B2 | 8/2006 | Tang |
| 7,234,940 B2 | 6/2007 | Weissman |
| 2002/0086263 A1 | 7/2002 | Kyung |
| 2003/0152431 A1 | 8/2003 | Jansen |
| 2003/0167061 A1 | 9/2003 | Schlegel et al. |
| 2004/0013999 A1 | 1/2004 | Sussman |
| 2006/0240378 A1 | 10/2006 | Weinstein et al. |
| 2006/0240379 A1 | 10/2006 | Weinstein |
| 2006/0275736 A1 | 12/2006 | Wen et al. |
| 2007/0269483 A1 | 11/2007 | Elia |
| 2009/0011382 A1* | 1/2009 | Bavar .................. 433/76 |
| 2009/0053670 A1 | 2/2009 | Koide et al. |
| 2009/0136892 A1 | 5/2009 | Marichi Rodriguez et al. |
| 2010/0137881 A1 | 6/2010 | Kamer |

OTHER PUBLICATIONS american-2, Drill Bushing Types-Definitions, All American Products Co., captured Mar. 31, 2006.

* cited by examiner

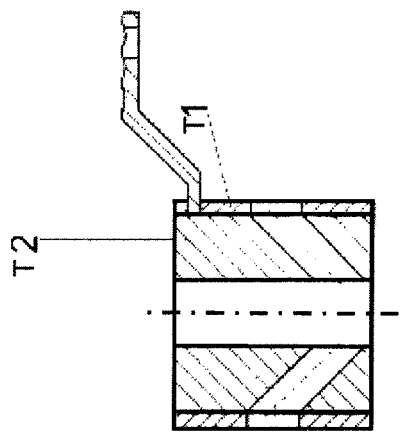
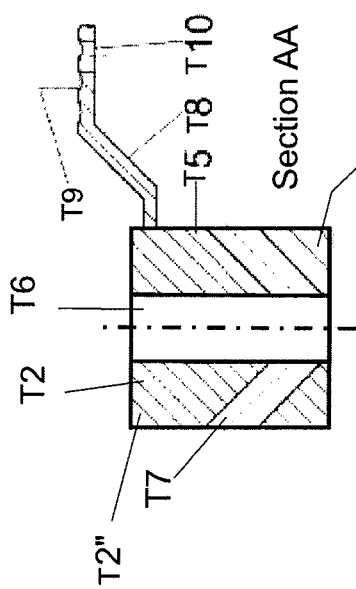
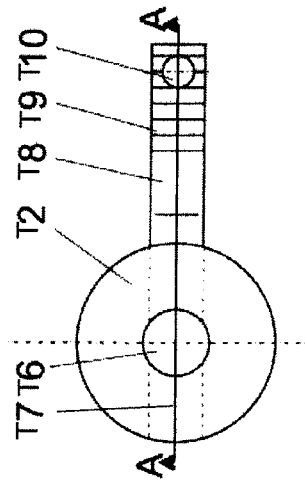
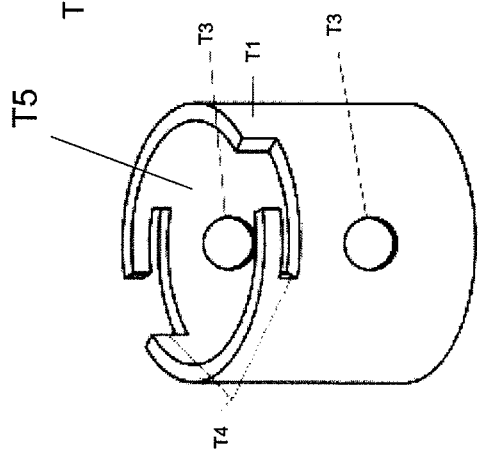
Fig. 13
Fig. 11
Fig. 12
Fig. 10

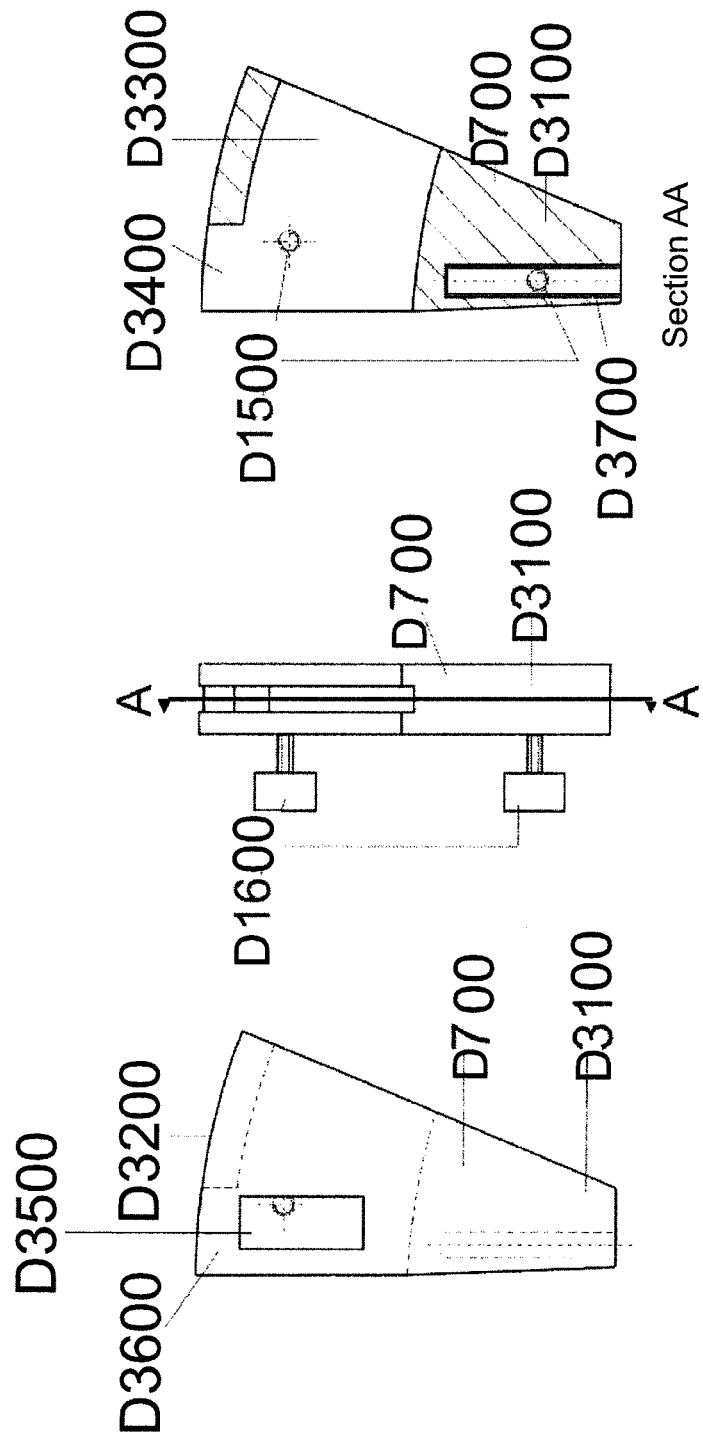

GUIDE TUBE POSITIONING METHOD IN POLYMERIC MATERIAL PLATE, TOMOGRAPHIC REFERENCE SUPPORT AND GUIDE TUBE POSITIONING DEVICE

This application is a continuation-in-part of U.S. patent application Ser. No. 12/248,377 filed on Oct. 9, 2008, currently pending, the entire disclosure of which is hereby incorporated herein by reference.

TECHNICAL FIELD

The present invention relates to a method for positioning of a guide tube in a plate to be positioned over the patient's mandible or maxilla, configuring a surgical guide, which allows for positioning the guide tube on the exact position so as to enable the drilling of a perfect hole in the patient's bone portion and subsequent positioning of the implant exactly on the planned spot.

The present invention further relates to a tomographic reference support, particularly for tomography use and/or to serve as a base for fastening one or more guide tube positioning devices, which enables planning with millimetric precision to determine the position for the positioning of one or more guide tubes in an acrylic plate or the like, configuring a surgical guide.

Finally, this invention relates to a guide tube positioning device, conceived to ensure the appropriate positioning of one or more guide tubes in an acrylic plate or the like, configuring a surgical guide.

STATE OF THE ART DESCRIPTION

The dental implant is commonly used to recover the appearance of the mouth of a patient who has definitively lost one or more teeth. The technique for performing a dental implant requires a number of procedural steps, until the implant is correctly and firmly positioned in place.

As it is known, besides enabling chewing and triturating foods into small portions (capable of going through the esophagus), the teeth play many important roles, such as the esthetic appearance that they confer upon people and also the influence they have in certain phonemes of speech, whose pronunciation is impaired in the absence of teeth. Therefore, the presence of teeth in one's mouth is very important.

Typically, the dental implant procedure comprises the use of a synthetic tooth (technically called a prosthetic crown), which must be positioned in the place of the original missing tooth, in order to restore the capacity of chewing and other properties attributed to the tooth, already described above. The dental crown is fixed to an implant, which in turn is positioned inside a hole made in the bone portion of the maxilla (upper arch) or the mandible (lower arch) of the patient's mouth.

The implant must be correctly and firmly fixed to the bone, so that the prosthetic crown will be as stable as a natural tooth. The conventional procedure of installing an implant comprises drilling a hole in the patient's maxilla or mandible, installing the implant and fixing the prosthetic crown to the implant. A plurality of types of implants are used, as for example cylindrical or threaded implants.

Describing in greater detail, implants are usually made of titanium alloy (due to the little reactivity, and the fast and comfortable association of the material with the bone tissue), and their upper portion comprises means for association with the prosthetic crown, so that the latter is correctly installed.

The procedure of boring the bone portion of the patient has to be well studied, since boring the orifice at an unsuitable site may prejudice the result of the implant, both from an aesthetic point of view and sometimes from a functional point of view, if fixing is made difficult due to the incorrect position of the orifice.

For the implant to the fixed correctly, the bone portion has to be drilled in the most suitable site. This orifice receives the implant, which rapidly interacts with the bone tissue and gets correctly fixed.

For implants applied to the lower alveolar bone (jawbone), it is necessary to be careful due to an aggravating factor, namely the presence of nervous tissue (lower alveolar nerve) in an internal cavity that passes through the bone; so it is essential to consider this situation when carrying out an implant procedure. Hitting or injuring the nerve will cause the partial paralysis in the patient's face, and this is untreatable once the paralysis becomes a permanent condition.

If the implant is carried out in the upper alveolar bone (maxilla), there is no major nervous termination, but instead up above is the maxillary sinus and the floor of the nasal cavity, which cannot be perforated at the risk of having the patient affected by severe hemorrhage. When these areas are perforated, it is generally necessary to make another perforation to position the implant in another orifice.

Therefore, the study of the correct site for boring the orifice must take into account a number of variables, such as the patient's bone constitution, the relationship with the neighboring teeth, the shape and positioning of the implant, potential bone loss resulting from inappropriate mouth hygiene, among others.

For carrying out this study, the professional resorts to clinical and imaging examinations, such as tomography and radiography, which enable an effective view of the bone constitution of the patient's face. However, especially when radiographic equipment is used, the images that can be obtained show distortions that prevent the unrestricted use thereof, for which reason the professional has to compensate for these distortions in order to achieve an efficient result.

In possession of these examinations, the professional makes a mold or model (generally from gypsum) of the patient's dental arch and, subsequently, makes a plate, generally of acrylic or acetate, which fits tightly and accurately into the mold. This plate may be made in various ways known to a person skilled in the art and ends up playing the role of a template for drilling the hole. After making the plate, a number of studies are carried out to, in the last analysis, position the drill or bur, in order to drill the hole correctly. However, in this step, without the use of a system that provides the data necessary for planning, often the only way to determine the positioning of the drill or bur is through the experience of the dental professional.

Because of the limited space in the patient's mouth, which renders the work of the professional hard, it is extremely difficult and error-prone to determine the correct positioning of the hole and make it without preliminary studies. Thus, a large percentage of dental surgeons carry out tomographic and/or radiographic procedures to—with the obtained images in hand—detect the bone constitution of the patient at the place where the implant will be fixed. Unfortunately, in this situation the professional does not perform a more accurate study of the correct positioning of the implant and performs drilling in the patient based on professional experience. Conventionally, this type of procedure is referred to as free-hand surgery.

It is important to realize that the free-hand implant is rarely positioned in an optimized manner, forcing the prosthetic crown to be built in a way that makes up for the misalignment caused by an inadequately installed implant. In the event of misalignments of about 1 millimeter or more, the crown may be compromised aesthetically or in terms of structural resistance.

Another risk in free-hand surgery is that the bur or drill used by the dentist may strike the maxillary sinus, the nasal cavity floor, neighboring tooth roots or, worse still, the lower alveolar nerve, which may cause severe consequences for the patient. To minimize this risk, the professional is generally over cautious with the depth of the orifices drilled, and it is not rare to see implants fixed with little depth. Such implants will certainly have decreased durability and will have a greater risk of loosening.

In free-hand surgery, the only way of getting to know the true bone anatomy of the patient, where the implant will be positioned, is by 'in loco' visualization—a lengthy procedure that considerably injures the gum tissue, positioned over the bone. 'In loco' visualization is achieved by carrying out various incisions in the gingival tissue, until the bone can be visualized.

After visualizing the bone, the professional has an idea of the position where bone drilling must be performed and, after placing the implants, he repositions the gingival tissue at its site, stitching it up afterwards. It is obvious that a major lesion to the gingival tissue causes pain and swelling for the patient, who in turn is the victim of an often painful post-operative process, requiring a great deal of analgesic, anti-inflammatory and antibiotic medicines.

Furthermore, dislocating the gingival tissue does not allow the surgeon to have the exact conception of the position and angulation of the roots of the fifteen neighboring teeth, which may cause accidents in these roots during the realization of the hole for the implant.

In order to solve the innumerous drawbacks of free-hand surgery, several techniques have been developed to determine more accurately the positioning of the hole to be drilled into the patient's bone portion for the positioning of the implant. In essence, the techniques can be divided in the computer-guided surgeries (surgical browsing), by prototyping, or based on plaster models.

Computer-guided surgeries (surgical browsing) use sophisticated and complex positioning and visualization electronic equipment in order to obtain the correct positioning of the orifice. Firstly, tomographic examinations are made of the patient's face, making it possible to obtain a series of images on the shape and bone constitution of the site where the orifice will be drilled. Once these values are obtained, the ideal positioning for drilling the orifice is achieved by using a software specific to each piece of equipment. The information on this positioning is fed into the equipment and various sensors are positioned inside and outside the patient's mouth.

During surgery, the professional handles the bur/drill facing a monitor, where he can watch his work. Together with the image of the patient's mouth, the professional is able to observe information on the positioning of the orifice being drilled. Such positioning is achieved from the interaction of the tool with the various sensors installed inside and outside the patient. Having information on the tool positioning, the equipment compares it to the information on the ideal positioning of the orifice. If the tool positioning strays from the ideally determined positioning, the equipment informs the professional of this divergence on the computer screen by means of light and/or sound signals.

Although the goal of this system is the positioning of the orifice with great accuracy, it has a series of drawbacks, such as the high complexity of the equipment involved, meaning high expenditures to acquire, operate, and maintain it; besides, there is a need for highly specialized personnel to operate it. Yet the major drawback of this process lies in the fact that no matter how precise is the control of tool positioning guaranteed by the sensors, it is unable to guarantee the precision of the boring, since the surgeon drills the bone directly without a plate or fixed template that prevents involuntary cross movement of the drill/bur. No matter how firmly he tries to grip the drill/bur, divergence can be inevitable because the tool is loose. Sometimes, a simple variation in the slant of the tool during boring is sufficient to deform the hole and alter its positioning, negatively affecting the accuracy of the work.

Denx® is an example of a company, among others, which has developed systems as the one described above. However, in short, the technology of computer-guided implant surgery has high costs and does not guarantee millimetric precision.

Surgery using guides obtained by the prototyping process has also been developed to guarantee the correct positioning of the orifice to fix the implant, with millimetric precision. Usually, the professional makes a first tomographic examination on the face of the patient needing an implant. Next, a second tomography is taken of a replica of the prosthetic planning containing radiopaque markers. This second tomography is essential due to certain characteristics of this kind of examination. If the patient has any kind of metal in his mouth (fillings, other implants, etc.), the result of the tomographic examination is altered in the places where the metal is located, generating punctual 'noises' in the image. In such cases, overlapping this examination and the tomography of the prosthetic planning replica containing radiopaque markers not only allows the gums to be visualized, but also provides a clear image of the places (teeth) where metallic elements are present.

The tomographic examination in the patient reveals the bone portion only and does not enable the measurement of the gum diameter, which means that it is necessary to do a second tomographic examination of the prosthetic planning replica containing radiopaque markers. Overlapping the two examinations through the radiopaque markers allows for checking the thickness of the gums and the dimensions of the bones, which will enable the correct positioning of the implant. Thus, as a first drawback, the need to perform two tomographic examinations (of the patient's face and of the prosthetic planning replica containing radiopaque markers) makes the process more expensive.

Having obtained the information on the bone at the site of the implant, the professional is able to plan the implant correctly, that is, he can determine the ideal diameter and depth of the orifice to be bored, and also determine its ideal position in the bone. This positioning is carried out by a software specific to each equipment.

Having obtained the information on the ideal positioning of the orifice, calculated by the professional using the software, a plate made of polymeric material is made in a prototyping equipment (widely known for use in other areas of expertise, such as engineering and medicine). This plate obtained already contains the shape of the patient's mouth (teeth, gums, etc., fitting perfectly therein) and comprises a correctly positioned drilling, that is, a hollow tubular metallic guide positioned on the orifice, so as to provide firmness to the drill/bur as it bores through.

Thereafter, the professional positions the plate on the patient's mouth, clasping it to the teeth/gums and positions a bur/drill inside the guide. As the guide is in the correct position, theoretically the bone orifice is bored with accuracy.

However, certain problems are associated with using the guide, which alone cannot ensure the desired accuracy in boring.

Though it is more precise than free-hand drilling, the fact is that when the boring end of the drill/bur passes through the guide, it tends to divert or bend while it sustains the load of having to bore the bone, and such diversion or bending are increased the greater the length of the free portion of the drill/bur which has passed through the guide, and the higher the bone density of the patient. As a result of this characteristic, let it be reiterated, the guide alone does not guarantee the necessary precision of the bone orifice.

Although many variations of this system have been conceived, all of these variations have the same concept noted above. Another major drawback in using the guides obtained by prototyping results from the fact that the equipment is very expensive and few pieces of equipment are available, which considerably increases the costs for producing this type of guide. Additionally, the time the dental surgeon must wait to receive the guide is very long (3 to 5 weeks on average).

Examples of companies which have developed such systems include Materialise® and Bioparts®, among others.

Finally, guided surgeries based on plaster models can be performed based on radiography and/or tomographic images. In using tomographic images, the professional (i) makes a mold of the patient's dental arch, (ii) makes a plaster model, (iii) fixes artificial teeth in the region where he intends to install the implants (iv), produces a replica of the plaster model with the artificial teeth, (v) produces a plate made of radiolucent material on the plaster models, (vi) inserts in this plate radiopaque markers pertinent to each kind of equipment, (vii) inserts radiopaque material (for example barium sulfate) in the cavities formed by the artificial teeth that were previously inserted into the model, thus obtaining a tomographic guide, (viii) installs the tomographic guide in the patient's arch, and finally (ix) performs a tomographic examination on the face of the patient in whom the implant is to be placed.

With the examinations in hand, the professional is able to use software to calculate the correct positioning of the orifice in the bone, always seeking to maximize anchorage of the implant and to cause no harm to the patient. After determining the ideal position of the implant, the professional positions the plaster model in a piece of equipment whose base slants in any direction on the horizontal plane and, in some cases, moves linearly horizontally. Next, the base is positioned with such a slant that a positioning element touches the plaster model in the ideal position (correct horizontal coordinates and slant) to bore the orifice. Thereafter, the positioning element is substituted by a drill/bur and an orifice similar to the one to be made in the patient's mouth in terms of positioning, angle and depth, is bored.

After boring the orifice, the professional positions inside it a component similar to the implant (implant analog) that will be performed. In some variations of the process, part of the site where the implant will be positioned is removed from the mold, but this is irrelevant for the exact definition of the technique. After placing the component similar to the implant, the professional fixes thereon a projecting guide that is projected beyond the implant, assuming the central positioning of the site where the original tooth would be located. As it could be no different, this projecting guide is a mark indicating the ideal spot for positioning the drill/bur for boring.

Thereafter, the professional produces a polymeric plate on top of the plaster model, which, evidently, will contour said projecting guide, and lastly it is sufficient to remove the plate and perforate the exact site where the definitive drill/bur guide shall be positioned. An alternative is that the projecting guide itself be in fact a drill guide and an integral part of the plate. In any case, the resulting acrylic plate will have an orifice with a guide in the exact spot where the patient's bone shall be drilled.

In the surgical procedure itself, problems similar to those already known in the state of the art also arise. The professional positions the plate on the patient's mouth, clasping it on the teeth/gums and positions a bur/drill inside the guide. Although it is more precise than free-hand drilling, the fact is that the boring end of the drill/bur, after passing through the guide, tends to divert or bend while it sustains the loading of drilling the bone. As a result of this characteristic, the guide alone does not guarantee the desired precision of the bone orifice.

Another drawback lies in the excessive number of steps needed until the orifice is bored, such as the positioning of the model, drilling of the model, insertion of the projecting guide, etc. The positioning of the plaster mold in the correct position requires a series of movements in the positioning equipment (many settings), which brings along an inherent inaccuracy: the greater the quantity of measurements and steps, the higher the chance that some measurement or positioning error occurs, no matter how minor it may be. And this accumulation of minor errors may cause a final error that is not negligible, which in practice occurs rather frequently. Such situation, in combination with the inherent inaccuracy of drilling due to the diversion or bending of the drill/bur, causes the final imprecision of the implant positioning—although lower than that of free-hand surgery—to have higher values than those desirable. Although diverse variations of these system have been conceived, all these variations have the same concept abovementioned.

As examples of this kind of system, we can mention Ray Set (Biaggini), GonyX (Straumann), TC Max (Ranali), MED 3D and Implant Logic System, among others.

In order to execute steps for carrying out the implant, particularly regarding accuracy in drilling the hole, a number of solutions have come up, some of which are mentioned hereinafter.

U.S. Pat. No. 7,097,451 refers to a thermoplastic template for making dental implants and a method for carrying out this procedure. The template comprises a malleable thermoplastic base and a rigid guide tube for positioning of the drill. The guide tube is fastened to the plate by means of a locking element. The base material is preferably any material having a softening and melting point at relatively low temperatures, concomitantly with high rigidity at room temperature, besides enabling malleability while it cools down to room temperature, at which moment the guide tube shall be positioned in an accurate manner. It should be noted that the main focus of the document is the constitution of the template, and it does not disclose how to determine the correct positioning of the drill guide.

U.S. Pat. No. 5,556,278 discloses a method for correctly positioning the hole of an implant by using a template and a positioning arm. However, due to the dimensions and weight of the arm, it is difficult to insert the drill and handle it to make the hole in the patient's mouth, even when he is anesthetized. This is a relatively rudimentary technique.

Document WO 2006/130068 refers to a tool for enabling the correct orientation of a drill or guide to make holes that enable the installation of a dental implant. Such an tool comprises two retaining arms which fasten it to the template, as well as guide arms, whose function is to determine the holes for boring the template. Afterwards, by applying the tool in the mouth of the anesthetized patient, the correct orientation is achieved by locating the template where the tool is oriented with the respective mark. With this, the system enables the drilling of the hole at the exact place where it shall occur, thus ensuring a successful operation. As a major drawback in this invention, there is the need to install the equipment in the user's mouth to check marking. And due to large dimensions, the patient will certainly feel uncomfortable, whether he is anesthetized or not.

U.S. Pat. No. 7,044,735 refers to a method for installation of a dental implant that includes the steps of positioning a guide tube adjacent the patient's bone and, after obtaining tomography images, creating a computer-aided image, so as to define the exact location for the hole where the implant will be positioned. Such system requires high financial resources due to the fact that it is mandatory to use tomography equipment, which cannot be afforded by the health units of most cities in regions that are less developed economically.

German document DE 202005008782 refers to the process of making a template, especially conceived for positioning drill guides to make implants, comprising at least one, but preferably two planes or fasteners for fastening X-ray films, a source locating light or a laser beam and an arm for performing the procedures necessary for correctly positioning the drill guide(s).

U.S. Pat. No. 5,015,183 describes a method that uses a radiopaque material installed in the patient's mouth, after which a large number of X-ray pictures are made so that one can determine the correct positioning of the hole in the bone portion of the patient. However, the large number of X-ray pictures required exposes the patient excessively and increases the cost of the procedure. This document discloses a quite sophisticated and costly piece of equipment for determining the correct positioning of the guide tubes, which excessively limits the use thereof at places with few resources.

Moreover, several configurations of guide tubes and positioning devices are currently known at the market, but each one of them has a certain kind of drawback or limitation, whether of technical or financial nature, limiting the use thereof in large scale.

Brazilian patent document PI 0301843-1, for example, refers to a constructive arrangement applied to a tube for surgical guide, where the tube comprises a first outer tube and a second inner tube having an upper flange. The second tube, which comprises a through aperture, is fitted inside the first tube and, joined together, they form a single device. By way of the through aperture of the second tube, a plurality of burs or drills is consecutively inserted and perforates the bone tissue of the patient until the final orifice is achieved. By substituting the second tubes for others having through apertures with ever larger diameters, it is possible to position burs with ever larger diameters, which will gradually widen the hole made in the bone tissue of the patient until its final configuration is achieved. The object of this document presents the drawback that, due to the reduced dimensions of the guide tube, the handling thereof is rather difficult and the inner tube may end up turning jointly with the drill/bur, constituting a dangerous situation and one that delays the conclusion of the procedure. Additionally, it may happen that the patient involuntary ends up ingesting or inhaling the element, which is dangerous.

The guide tube that is the subject matter of document PI 0301843-1 does not avoid diversion or bending of the drill when boring the bone tissue, not guaranteeing a maximum precision in boring the orifices to place implants.

Regarding the positioning devices, which also may or may not contribute to the correct positioning of the implant with much accuracy, a plurality of devices were proposed, each seeking to solve the problem of the correct positioning to perform drilling and assembly of the implant guide; yet, as a general rule, they are decidedly complex, expensive, heavy and hard to handle.

The state of the art of positioning devices is generally represented by U.S. Pat. No. 6,634,883, which reveals a positioner having a rigid base, and a column that projects from this base and that supports a main head. The column has mechanisms that enable the regulation of the height of the head. In turn, the head comprises two main portions angularly moveable that comprise locking mechanisms in the most diverse positions and visual indicators of angle position (angle in relation to a given vertical or horizontal reference). One of the two main portions also comprises means (preferably threaded) to fix the positioning guide.

The equipment that is the subject matter of U.S. Pat. No. 6,634,883 presents higher costs, dimensions and weight and a relative complexity (many settings) in relation to the device covered by the present invention.

Another known conceptually similar positioner, already mentioned previously, uses a fixed guide in an "L" shaped rod or the like and a base having a movement capacity (slant) in any direction on the horizontal plane and also linear horizontal movement. As soon as the plaster model is positioned on the base, the base is positioned with such a slant that a positioning element touches the plaster mold in the ideal position (correct slant and horizontal coordinates) to bore the orifice. Thereafter, the positioning element is substituted by a drill or bur in a drilling machine attachable to the device for boring the orifice in the plaster model.

All the kinds of surgery abovementioned, to a greater or lesser degree, show inaccuracy in the positioning of the dental implant, which makes it difficult to create and subsequently position the prosthetic crown.

If the positioning of the implant is excessively wrong, the consequent difficulties in making a suitable and functional prosthetic crown are innumerous, since the dentist will be unable to position it symmetrically on top of the implant. In such cases, generally the implant is positioned with a very inaccurate slant and consequently the main portion of the prosthetic crown (which imitates the tooth per se) needs to be quite distant from the place where it is fixed to the implant. The result is the occurrence of a leverage effect that will certainly shorten the useful life of the part to a considerable degree, generating constant interventions.

Another drawback in such cases is the difficulty in brushing and cleaning due to the very irregular shape of the crown, causing the early accumulation of dental plaque and its collateral consequences (bad breath, inflammation of the gingival tissue with consequent bone loss and, finally, the short durability of the implant).

If the positioning of the implant is wrong to a lesser extent, in many cases it will still be necessary to cement the crown in the implant, which will prevent its removal without its destruction. Generally in such cases, the crown ends up taking up a shape that is little symmetrical in order to avoid that, once it is installed, it pressures the adjacent teeth too much, which would cause bone re-absorption (property of the alveolar bone to reabsorb material when something anchors onto it under pressure, so that the pressure ceases). In other words, when a crown is installed under pressure against another tooth, it ends up forcing the implant, and the bone portion at the site where the implant compresses the bone is reabsorbed, significantly decreasing its stability.

In short, although there are several technologies for making dental implants with accuracy in the drilling of the patient's bone portion, most of them use sophisticated equipment and computer-aided measuring equipment, which are unaffordable by the health units in most regions that are less developed economically. Others resort to methods that use relatively simple equipment, but which, when requiring a too toilsome process and mainly because they do not provide means that guarantee the security of the data obtained, end up casting doubt on the safety of the method.

Thus, so far there has been no developments of tomographic reference supports comprising the possibility of carrying out tomographic exams and also allowing, in an easy, fast and precise way, the placement of the guide tube positioning device with accuracy, without the need of heavy investments in high-technology devices and which were easy to be used by dentists.

More specifically, there has been no development of a positioning device that reduced and/or eliminated fruitless steps for the correct positioning of the guide tube on a plate (configuring a surgical guide) to be positioned on the patient's mandible or maxilla.

Although there are several guide tubes and their positioners on the market, no positioning device has been created that showed effective constructive simplicity and low-cost manufacture, besides from offering impeccable and easy manageability and performance, so as to present possibilities of large-scale application, enabling guided surgery to be performed with truly millimetric accuracy, which is an unprecedented fact not yet achieved systematically and on a mass basis.

Finally, there has been no development of any method for the positioning of a guide tube on a plate, configuring a surgical guide which, with simplicity, efficiency and extremely high accuracy, allowed for positioning the tube on the exact position, so as to enable the drilling of a perfect hole in the patient's bone portion and the subsequent positioning of the implant exactly at the planned space.

PURPOSES OF THE INVENTION

The purpose of the present invention is to provide a guide tube positioning device that is simple to manufacture, easy to operate, accurate and efficient, and which has a low purchase cost, to enable the positioning of any guide tube already known in a plate or template for a dental implant, forming a surgical guide, with great accuracy.

Another goal of the present invention is a tomographic reference support, especially for tomography use and/or to serve as basis for the fastening of one or more guide tube positioning devices, and which allows planning to determine the position for making the hole for installation of the implant with millimetric precision and which has low acquisition cost, so as to enable its use even by the health units of economically less-favored regions.

A goal of the present invention is also a method for positioning a guide tube in a plate, configuring a surgical guide which allows, with simplicity, efficiency and high accuracy, the positioning of the tube in the exact position, so as to enable the boring of a perfect hole in the patient's bone portion and the later positioning of the implant exactly on the planned spot.

BRIEF DESCRIPTION OF THE DRAWINGS

The present invention will be described next in greater detail based on a sample embodiment represented in the drawings. In the drawings:

FIG. 10 is a perspective view of the outer tube segment of the guide tube that is the object of the present invention.

FIG. 11 is a cut side view of a first embodiment of the inner tube segment of the guide tube that is the object of the present invention.

FIG. 12 is an upper view of the inner tube illustrated in FIG. 11.

FIG. 13 is a cut side view of a first embodiment of the guide tube that is the object of the present invention, in operating position.

FIG. 25 is a sixth partial view of the guide tube positioning device that is the object of the present invention.

FIG. 26 is a seventh partial view of the guide tube positioning device that is the object of the present invention.

FIG. 27 is an eighth partial view of the guide tube positioning device that is the object of the present invention.

DETAILED DESCRIPTION OF THE DRAWINGS

Figure 1:
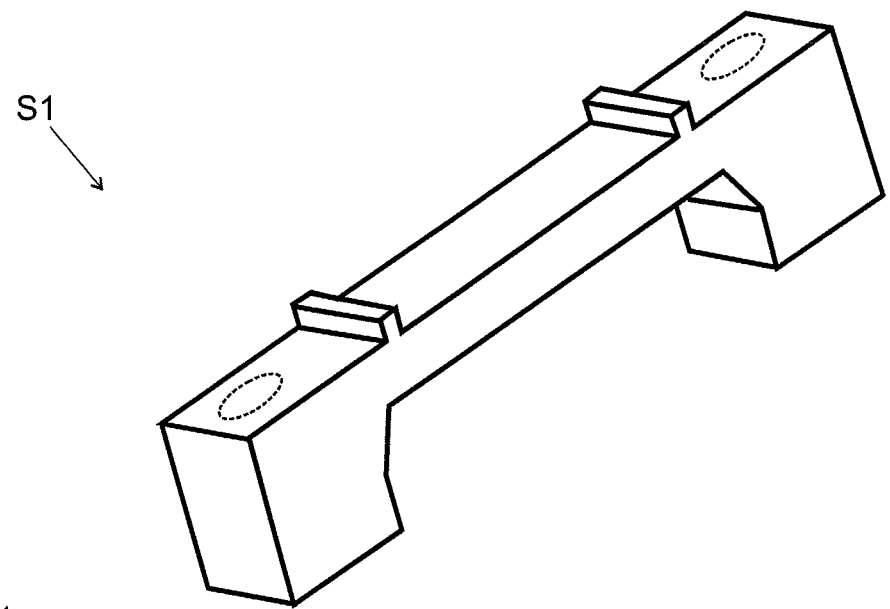
FIG. 1 is a first schematic view of a first embodiment of the tomographic reference support according to the present invention.
Figure 2:
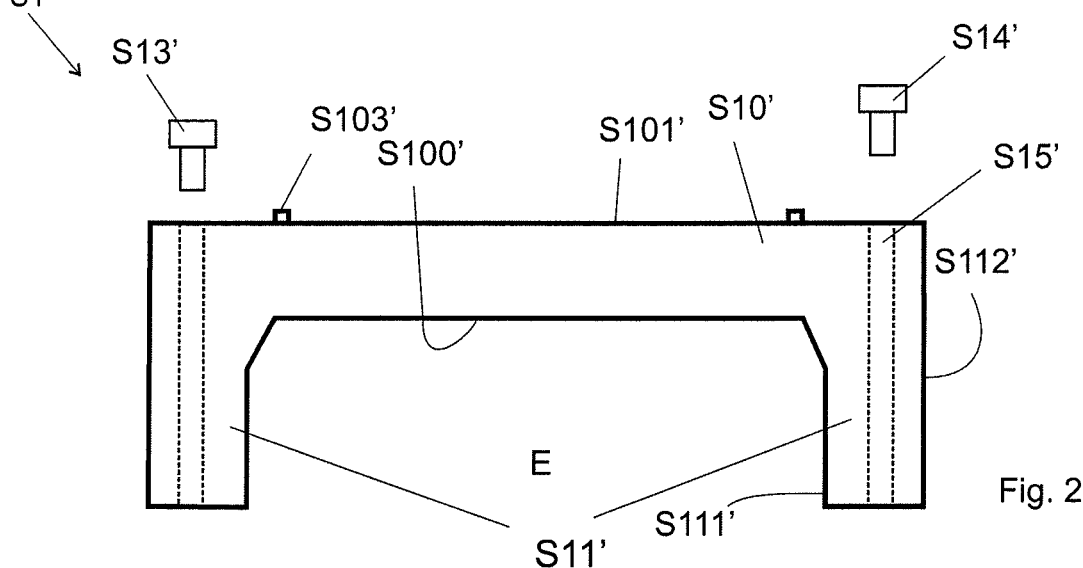
FIG. 2 is a second schematic view of the first embodiment of the tomographic reference support according to the present invention.
Figure 3:
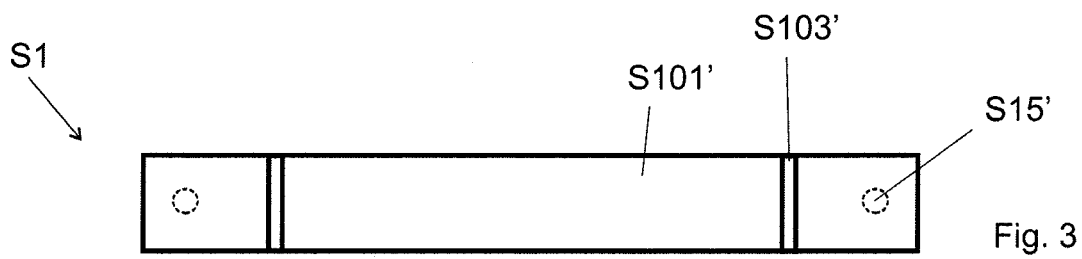
FIG. 3 is a third schematic view of the first embodiment of the tomographic reference support according to the present invention.

The present invention refers to a tomographic reference support and a guide tube positioning device that enable to determine the place for making the hole with millimetric precision, without the need to use expensive equipment and other computer-aided pieces of equipment, as well as to position the guide tube in an acrylic plate, configuring a surgical guide, with great precision given the calculated position.

Thus, this technology is especially ideal for professionals who work in economically less developed regions or far away from cities/urban centers.

To facilitate description, a first configurative variation of the tomographic reference support covered by this invention will be hereinafter called 'support' S1. A second configurative variation of the tomographic reference support covered by this invention will be hereinafter called 'support' S2.

The supports S1 and S2 have the major role of tomographic reference to enable the exact determination of the positioning of one or more surgical guide tubes with millimetric precision in an acrylic or acetate plate, configuring a surgical guide which will enable one to make one or more holes in the patient's bone tissue and to correctly position one or more implants. The supports S1 and S2 also have the role of serving as a base for fastening at least one guide tube positioning device D5 which is covered by this invention and will be described in greater detail later.

Preferably, the support S1 comprises a body shaped substantially as an inverted "U", defining a first main portion S10' having two free ends, a respective prolonged orthogonal portion S11' (configuring the 'legs' of the "U") extending from each end.

The first main portion S10' and the two prolonged orthogonal portions S11' define a space E which will be occupied by the anatomic mandible or maxillary portion when the support S1 is installed in the patient's mouth or in a model corresponding to the dental arch of this patient.

Further detailing the description, the first main portion S10' comprises a first surface S100', facing the space E defined and an second surface S101', opposite. Analogously, each one of the prolonged orthogonal portions S11' comprises a first surface S111' facing the space E defined and an second surface S112', opposite.

Preferably, the prolonged orthogonal projections S11' have the same length and are substantially parallel to each other and substantially perpendicular to the main portion S10', but it is evident that the geometric details may vary freely, after all the anatomy of the maxilla and of the mandible vary widely from person to person. It should be pointed out that the protection defined for the present support S1 lies in its concept, not in its specific geometric constitution.

Also preferably, the second surface S101' of the first main portion S10' comprises one of more fitting elements S103' which prevent the guide tube positioning device from turning when the guide tube is attached to the support S1. Preferably, two substantially transverse, rectangular projections S103' are provided and they are positioned symmetrically and equally distant from each other.

Preferably, the support S1 does not comprise channels for making gingival sounding, since the tomographic examination itself precisely indicates the anatomy of the bone where one wishes to install the implant. However, it is perfectly possible for the support for tomography use to have such channels to enable the performance of soundings.

In the support S1, there are also first and second radiopaque elements S13' and S14', in the preferred form of two radiopaque screws, positioned in holes located in the prolonged orthogonal portions 511'. Preferably, the screws are inserted into two threaded holes S15', positioned adjacently to the free ends of the first main portion S10'. Also preferably, the threaded holes S15' get into the two orthogonal projections S11', as it can be seen in the respective figure. It is evident, however, that one may use any other types of radiopaque elements, as suitable or desired.

The two threaded holes S15' are further used for association of the guide tube positioning device (or any other), insofar as they receive the system for fastening it, and the result is a rigid, tight-fitting and secure fixation. Finally, it should be noted that the threaded holes S15' may be substituted by any other means for functional association.

In order to carry out the procedure, the support S1 has to be positioned/mounted on a polymeric material plate, molded from the patient's dental arch which serves as a template, as previously discussed. The support S1 is fastened to the base by any radiolucent joining agent, as for example, self-polymerizing acrylic resin. The assembly of the support S1 on the plate configures a surgical guide.

The assembly of the support S1 on the plate is made on a tomographic mounting frame, which will be described later. After assembling the support S1 on the tomographic mounting frame, one fixes a prosthetic crown of a radiopaque material (not illustrated) to the second surface S101' of the first main portion S10', for the execution of the tomographic examination(s).

It is important that the support S1 be positioned and fastened to the plate with great accuracy, in order to avoid mistakes that misrepresent the positioning of the implant and, because of that, the use of the tomographic mounting frame is essential.

Through the pre-fixed dimensions of the support S1, the radiopaque screws S13' and S14' and the radiopaque crown, it is possible to obtain images of great precision, and the tomographic examination enables one to provide the millimetric positioning of the guide tube on the plate/template, which will result in making a hole for fixing the implant perfectly positioned.

Analogously to the support S1 described in details above, the second configurative variation of the tomographic reference support, namely support S2, has the main function of tomographic reference to enable the exact determination of the positioning of one or more surgical guide tubes with millimetric precision, which will allow for boring one or more holes in the patient's bone tissue. The support S2 also serves as a base for fastening guide tube positioning devices, but it has a more enhanced shape which facilitates the use thereof and the perfect positioning of one or more guide tubes on the acrylic plate.

The support S2 allows for correctly preparing the surgical guide more easily than the support S1, being an important enhancement thereof.

Preferably, the support S2 comprises a flat (i.e., planar) body defined by a substantially trapezoidal isosceles shape, whose ends of its bigger base have a convex shape which define two portions delimited by two projecting semi-circles S20 and S21, so as to ensure that this single shape of plate can cover and overlap the shape of any dental arch. In fact, all geometry of the support S2, and not only the projecting semi-circles S20 and S21, was conceived so that it can be used by any adult patient or someone having a very well developed facial/oral constitution and dental arch. In any case, nothing prevents one or more shapes of support S2 from existing so that a greater spectrum of patients can be served.

In details, the support S2 comprises a side surface having rounded edges S22 substantially protruded S23 from a first portion of said first semi-circle S20 up to a second portion of said second semi-circle S21, delimiting the surface that defines the smaller base from the body of the support S2. Essentially, the shape of the support S2 is in "C", or "half moon", so as to cooperate with the oral cavity and the dental arch of the patient.

Also preferably, the support S2 has five cylindrical protuberances S24 having through-openings (also referred to as "fixing orifices") concentric with the respective cylindrical protuberances. Said protuberances S24, which are optional, as opposed to the mandatory through-openings that they enclose, are arranged over the body of the support S2, so that, preferably, four protuberances are arranged adjacently to the side ends and only one of the protuberances is arranged more centrally in relation to the surface that defines the bigger base from the body of the support S2, next to the place that defines the middle portion of the patient's tongue. The through-openings extend vertically through the body when the body is positioned with a plane of the body oriented horizontally.

A radiopaque element S25 (not illustrated) is associable with each one of the through-openings defined by the cylindrical protuberances S24. Preferably, each radiopaque element S25 has the form of a radiopaque screw, vertically positioned in localized holes, and their function is to determine a horizontal plane upon the analysis of the tomographic images.

The screws S25 enter into the through cavities in threads provided therein (in the cylindrical protuberances S24, when they exist) until complete locking. However, it is evident that the number and the positioning of radiopaque test specimens may vary as necessary and/or desirable, as long as they enable the visualization/determination of a single horizontal plane among them. In view of that, the minimum amount of radiopaque screws to be threaded on the support is three (since three points define a plane).

The lower surface of the body of the support S2 further has marks that act as coordinates to identify the most appropriate hole for the installation of the guide tube positioning device.

The support S2 further comprises fitting elements, as auxiliary orifices S27 that cooperate with the respective projections in the positioning device in order to prevent it from rotating when associated with the support. Preferably, the auxiliary orifices S27 are positioned adjacently to the cylindrical protuberances S24. It is important to clarify that the number and positioning of the orifices S27 may vary as necessary and/or desirable. Furthermore, the orifices S27 can be replaced by any other means for functional association.

To carry out the procedure, the support S2 must be positioned/assembled over a polymeric material plate molded from the patient's dental arch which serves as a template and which is already known by those skilled in the art. By the way, the plate/template can take on any desired or necessary configuration (primarily in view of shape of the patient's dental arch) and be made in any material and, also, be obtained by means of any desired manufacturing process, since such variables are irrelevant to determine the protection scope of the invention.

Preferably, the upper surface of the support S2 is fastened to the plate/template having at least one prosthetic crown of radiopaque material (not illustrated) for the execution of the tomographic examination(s).

The fastening between both occurs through the use of any radiolucent joining agent, such as self-polymerizing acrylic resin. It is important to clarify that the positioning of the support S2 on the acrylic material plate does not need to be previously defined or very accurate, as it is sufficient to have the plate placed only adjacently to the protuberances S24 comprised by the body of the support S2.

Through the pre-fixed dimensions of the support S2, the radiopaque screws S25 and the radiopaque crown, one can obtain images of great accuracy, and the tomographic examination (whose steps will be described later) enables one to provide the millimetric positioning of the guide tube on the plate/template, which will result in making a hole for installing the implant perfectly positioned.

The present invention also foresees that, in the end of the tomographic examinations, the support S2 be optionally cut with, for instance, a bur, so as to adjust the body of the support S2 to the plate/template and go on with the procedure of installation of the implant. On the other hand, it shall be highlighted that the trapezoidal shape of the support S2 was especially designed so that it could be adjusted to the patient's mouth during the examinations and/or installation of the implant, without, for such purpose, having its ends necessarily cut out.

It should be noted that there are a number of known pieces of equipment for making surgical guides for dental implants (Ranalli/TC-Max, GonyX (Straumann), Biaggini/Ray Set, IVS-Solutions/GonyX, Med 3d, Cadimplant, among other others known to those skilled in the art), in which it is imperative to use some reference device that produces radiopaque tomography images that will serve as a base for making the mathematic calculations necessary to determine the ideal position of the planned implant.

However, in the case of the reference devices used by the already known equipment, in order to use these successfully, the model of the patient's dental arch must be assembled on a base of the device and attached to it by means of gypsum or mechanically. This process requires special care in preparing the gypsum model (special cutouts in the base of the model), and positioning and aligning the model correctly with respect to the device. In addition, the attachment with gypsum takes considerable time and consumes material (the gypsum itself used in the joining process).

The equipment that will receive the model shall have an appropriate base and complex mechanical resources, so that the model can make movements of rotation, inclination and linear sliding. Besides, it is necessary to calculate mathematically the extent of these movements and carry them out with accuracy. Such complicating factors mean an increase in the cost of industrial production of the equipment, in time and in the complexity of the work of the professional, besides meaning a collateral increase in the probability of failures.

The use of the tomographic supports S1 and S2 also produces the images necessary for planning, but it greatly simplifies the work, since the steps listed below are eliminated:

there is no need for special preparation of the gypsum model (specific cutouts in the model base);

no gypsum is used in the process of joining the gypsum model to the guide tube positioning device;

there is no need of mechanical resources on the guide tube positioning device for retaining the gypsum model, since both tomographic supports S1 and S2 directly receive the guide tube positioning device (it is impossible to observe inaccuracy in the position of one in relation to the other);

there is no need to make mathematical calculations for alignment with the guide tube positioning device, since both tomographic supports S1 and S2 automatically align the guide tube positioning device (there is no risk in positioning it incorrectly, due to the existence, respectively, of the rectangular projections S103' or the orifices S27); and there is no need to build a base on the guide tube positioning device to receive the model, nor is there any need for the presence of complex mechanical resources to move the model.

The supports S1 and S2 may be made of any necessary or desirable radiolucent material, and all the variations are included in the protection scope of the invention.

Continuing the description of the present invention, the mounting frame previously mentioned is preferably used together with the support S1, making it possible to correctly align the support over the plate/template. After all, there is no advantage in the accuracy of tomographic examinations if the respective support S1 is positioned in misalignment with the plate/template (and, at last analysis, with the dental arch and the bone to be drilled for placing the implant), since it is this that ensures the correct positioning of the support S1 on the polymeric material plate.

To facilitate description, the mounting frame of tomographic support covered by the present invention will be hereinafter referred to as "tomography mounting frame" (or simply "mounting frame") M4.

The mounting frame M4 is, in essence, an adjustable structure designed to enable the assembly, in the specific case, of the tomographic support S1 in correct alignment in the respective polymeric material plate/template. The mounting frame M4 comprises a base 40 having at least three leveling elements M41, which enable inclination of the base in any desired direction.

Preferably, the leveling elements are screws M41 that can be threaded into holes provided in the base M40, but it is evident that other means may be employed, such as individually adjustable telescopic projections, or also any other solution that is functional and reliable. Also preferably four screws M41 are used, each one positioned at a corner of the base M40, which is also preferably square.

Associated with the base, a column M42 is provided, perpendicular in relation to base M40, from the upper free end of which a substantially horizontal arm M43 extends. The arm M43 can move rotationally with respect to the column. The arm M43, in turn, has a support carrier M44, which is inside a through bore positioned adjacent its free end and the movement of which is limited by a horizontal locking screw M45.

The support carrier M44 is preferably constituted by a vertical rod M440 fixed at the lower end to a horizontal base M441 having vertical bores M442 through which the carrier pin M443 (preferably two) runs, threaded in the upper end and frontally locked by means of a locking screw M444.

Evidently, such a constructive configuration is merely exemplary, since the column, arm and support carrier may have the most varied shapes and be associated to each other in other manners rather than that described in the previous paragraph.

In order to position correctly the tomographic support S1, the screws M41 enable the accurate leveling of the base, while the rotation motion between the column M42 and the arm M43 enables greater comfort in positioning the model of the patient's dental arch (gypsum model) with the plate/template installed.

The carrier pins M443 can move vertically and rotationally, enabling precise adjustments in the operation of mounting the tomographic support S1.

The vertical bores M442 of the horizontal base M441, in turn, have distances from each other corresponding to the size of the tomographic support S1 to be used.

Therefore, the movement of the components of the mounting frame M4 guarantees the assembly of the tomographic support S1 in correct alignment on the respective plate/template of polymeric material, since both the acrylic plate (positioned on the plaster mold, which in turn is positioned on the base M40 of the mounting frame M4) and the column M42, rod M43 and by interference the support S1, will be in perfect angular horizontal alignment.

In the case of using the support S2, the mounting frame is not necessary, since this support defines one plane because it has three or more radiopaque elements.

The present invention further refers to the previously mentioned guide tube positioning device (which will be described later on) which enables the positioning of one or more guide tubes for the installation of a guided implant with millimetric precision in boring the orifice for positioning of the implant. The precision achieved by this technique is proved to be 0.3 millimeter (mm).

The present procedure begins with the exact determination of the positioning of the implant to be performed. This determination is preferably carried out by analyzing the tomographic examinations performed on the face of the patient.

In the tomographic examinations, firstly the professional makes a plaster model of the patient's dental arch and, based on it, he makes a plate made of polymeric material (usually acetate or PVC thermoplastic). This plate is widely known in the field of odontology, is easy to make and the cost is low, quite the opposite of the highly expensive plates obtained by the already mentioned prototyping process. The tomographic support S1 or S2 is installed on this plate. The plate made of polymeric material containing the tomographic support S1 or S2, with the respective vertical screws and the radiopaque tooth, is fastened on the dental arch of the patient and the face of the patient is scanned in the tomograph.

The images resulting from the tomograph, in the region in question, will show all the bone characteristics, the neighboring teeth, the radiopaque tooth (which, on examination, will have the appearance of a regular tooth, as if it were present) and the vertical radiopaque screws present in the tomographic support S1 or S2 (which, in the case of the support S2, are three in number and are parallel in relation to one another and have the same height, defining a horizontal plane).

The professional can then require the computer program to cut images parallel and perpendicular to the plane determined by the respective vertical radiopaque screws. Since the tomographic support S1 or S2 is positioned on the same plane in relation to the acrylic plate (defined by the radiopaque screws or the like), this condition is guaranteed and a series of geometrically precise images can be generated. As such images are perpendicular and parallel in relation to the bone, there is no deformation of the measures highlighted, and the planning of the positioning of the implant can be ideal.

Holding the images perpendicular and parallel to the bone in the implant region, the professional can simulate/position the implant on the ideal position and size over the images, based on the thickness of the bone tissue, positioning of the nerve, of the maxillary sinus or of the floor of the nasal cavity, the position of the neighboring teeth and also the ideal position of the tooth to be implanted (simulated by the radiopaque tooth installed on the tomographic support).

In view of the surgical planning, the computer program generates figures corresponding to the ideal positioning of the orifice, namely, the transversal position in relation to the bone (referred to as the vestibular-lingual distance), the transversal angle in relation to the bone (referred to as the vestibular-lingual angle), the longitudinal position in relation to the bone (referred to as the mesio-distal width), the longitudinal angle in relation to the bone (referred to as the mesio-distal angle) and its depth in the bone.

In possession of these figures, the ideal position for the orifice is formed, and the next step is to install the guide tube in the plate/template, in this exact planned position, so as to position/conduct the surgeon dentist's bur or drill with accuracy while drilling the bone.

In a non-limiting preferential embodiment, the guide tube comprises at least a first outer tube segment T1, having a first axial through aperture T5 and at least a second inner tube segment T2, having a second axial through aperture T6, the second tube segment T2 being inserted inside the first axial through aperture T5 of the first tube segment T1.

It is the outer tube segment T1 that is fastened to the polymeric plate after having been correctly positioned by the positioning device D5, such as described below, forming the surgical guide.

The inner tube segment T2, in its turn, is also known as a reduction tube, because it tightly adjusts to the diameter of the bur or drill, which is inferior.

Evidently, for said situation to be executable, it is essential that the inner diameter of the first axial through aperture T5 be substantially equivalent to the outer diameter of the second tube segment T2. If there is an excessive slack between both, the second tube segment T2 may present a radial slack inside the first aperture T5, which will make execution of the orifice in the bone of the patient more imprecise, as it will be mentioned below. On the other hand, in a situation in which the second tube segment T2 enters with much interference inside the first aperture T5, the functionality is prejudiced, since it will be necessary to apply much force for such purpose.

Preferably, both outer and inner tube segments T1 and T2 present circular transversal section, although, in certain specific circumstances, other formats may be idealized.

The outer tube segment T1 also comprises at least one lateral through orifice T3, substantially cooperative with at least one respective third through aperture T7 provided in the inner tube segment T2, as it can be easily seen in the drawings.

When the inner tube segment T2 is inserted inside the first axial through aperture T5 of the inner tube segment T1, in a locking position, the lateral through orifice T3 and the third through aperture T7 radially slanted become axially aligned.

The so-called locking position is that where there is no angular movement of the inner tube segment T2 in relation to the outer tube segment T1, and corresponds to the working situation of the guide tube, to be explained below. Alternatively, there may be a configurative variation of the present guide tube where a slight angular movement is provided, as long as this movement does not completely misalign the side through orifice T3 and the third through aperture T7.

Also preferably, the outer tube segment T1 comprises two lateral through orifices T3 positioned on its median line and diametrically opposite, exactly as illustrated in figure T1, although this is just one of the many possible variations.

In the preferred case, in order to cooperate with the two lateral through orifices T3 positioned medially and diametrically opposite, the inner tube segment T2 comprises two third through apertures T7 diametrically opposite, each having a first end portion positioned on the median line of the outer wall of the inner tube segment T2.

Preferably, the third through apertures are downwardly slanted, that is, each one comprises a second end portion positioned in the lower portion of the wall that defines the second axial through aperture T6.

It is important to reiterate that the shape, geometry, positioning and quantity of through orifices T3 and third through apertures T7 may vary freely without excluding the resulting guide tube from the scope of the attached claims.

Another characteristic of the guide tube lies in the fact that the outer tube segment T1 comprises at least a locking means that preferably, but not compulsorily, assumes the shape of a slot with radial entry T4, located at its upper end portion. Obviously, other shapes and arrangements of the locking means can be provided, as long as they are functional.

More preferably, the outer tube segment comprises two slots with radial entry T4, diametrically opposite, such as illustrated in FIG. 1, although its specific shape may vary freely.

Another characteristic of the guide tube provided in this invention, and which especially facilitates its installation, use and operation, is the existence of at least a means for handling and positioning T8, which is preferably latch-shaped, substantially linear and slanted, which is projected radially and upwardly from the outer wall of the outer tube segment T2. Obviously other variations can be used, if necessary or desirable.

Preferably, the latch T8 comprises an end surface having a through hole T10 and knurled surface finishing.

It is obvious, however, that the shape of the latch T8, the quantity thereof, its surface finishing and various other characteristics may vary freely, without excluding the resulting invention from the protection scope of the claims.

To assemble the guide tube, the outer tube segment T1 is installed and fixed on the plate of polymeric material, in the determined position, a procedure that has been explained above. This outer segment is placed in the ideal position calculated so that the bone orifice is perfect, by means of the guide tube positioning device which is also the object of the present invention and will be described in detail further ahead.

Then, the outer tube segment T1 is positioned over the exact site where the dental implant will be installed.

After the outer tube segment T1 has been fastened, the next step is to place, install and fix the inner tube segment T2 inside the first axial through aperture T5. After having been inserted inside the aperture T5, the outer tube segment T2 is angularly rotated until the latch T8, or the like, penetrates into one of the slots T4. After this penetration, the movement ceases and, due to the shape of the slot T4, the latch is prevented from moving even in the opposite direction, unless an upward force is applied thereto.

Preferably, the slots T4 have such a geometry that the latch T8 only penetrates inside when the inner tube segment T2 is moved angularly clockwise. Said situation is preferred since the drills and burs that bore the bone orifice (not illustrated) also rotate clockwise, and the unintentional or accidental unlocking simply cannot occur. Such situation, however, is merely optional.

Due to the preferred existence of two slots diametrically opposite and a single latch T8, the professional can choose into which of the two slots T4 he wishes to perform locking, which can be very convenient since the latch T8 has the additional function of facilitating the positioning of the inner tube segment.

Moreover, it is important to note that said orifice T10 existing in the latch T8 serves to tie a surgical wire in order to avoid swallowing or accidental inhaling of the inner tube segment T2 in the unlikely situation in which it has become unattached and left its position inside the first through aperture T5.

Finally, it is worth noting that the major function of the knurling existing on the latch T8 is to facilitate friction (grip) of the tool used by the professional to position it inside said aperture T5.

Figure 4:
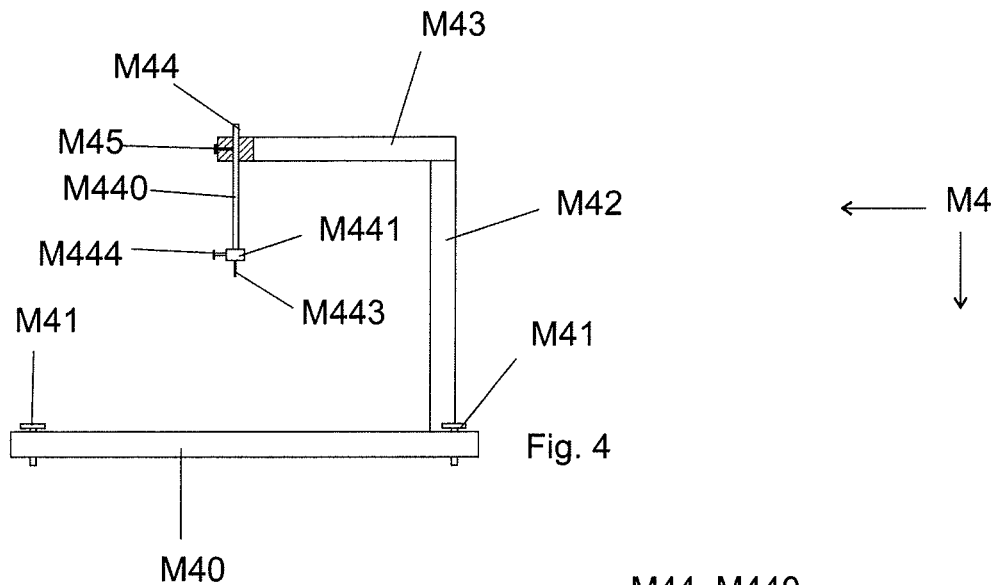
FIG. 4 is a first schematic view of the mounting frame for the first variation of the tomographic reference support according to the present invention.
Figure 5:
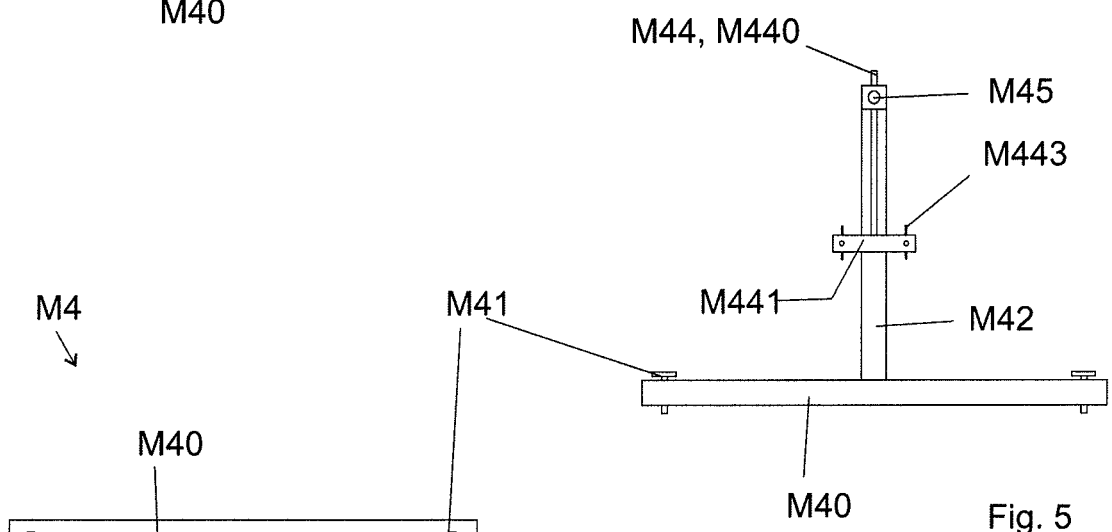
FIG. 5 is a second schematic view of the mounting frame for the first variation of the tomographic reference support according to the present invention.
Figure 6:
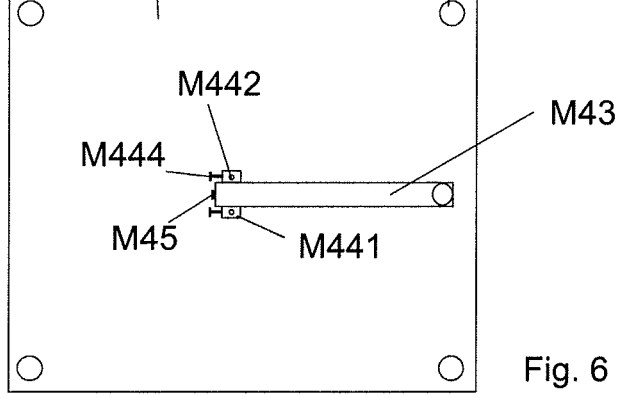
FIG. 6 is a third schematic view of the mounting frame for the first variation of the tomographic reference support according to the present invention.
Figure 7:
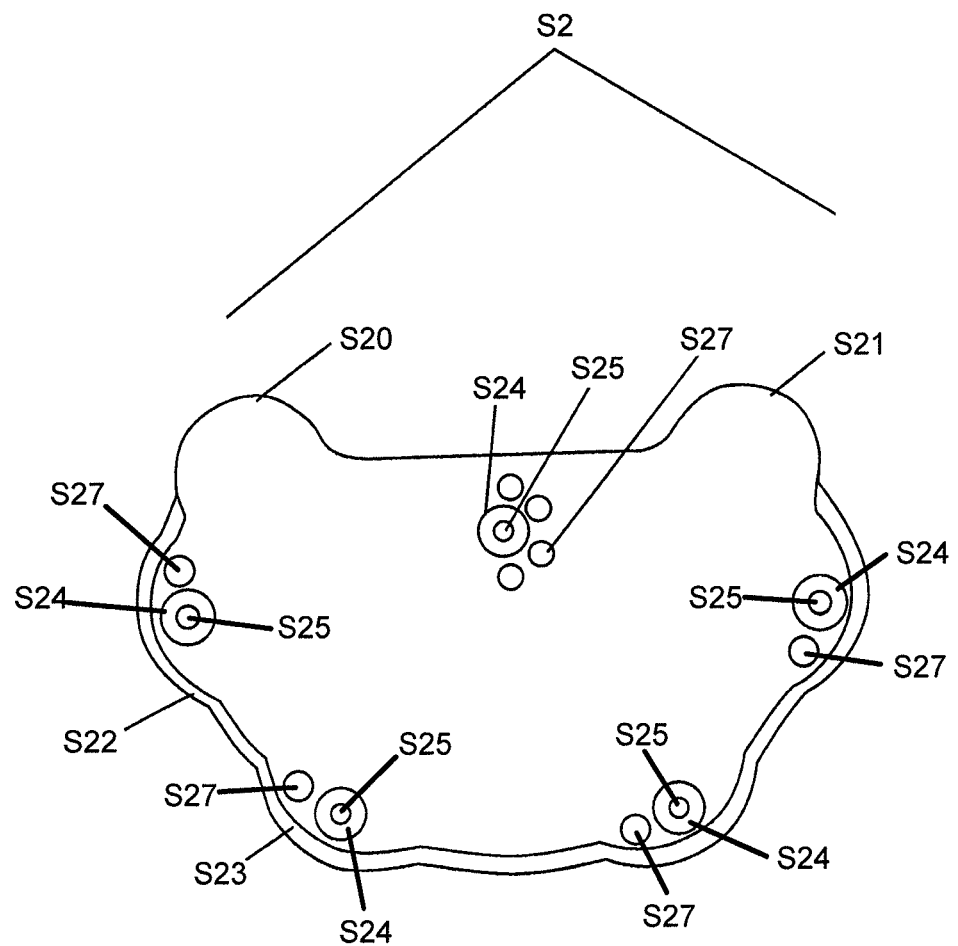
FIG. 7 is a first schematic view of a second embodiment of the tomographic reference support according to the present invention.
Figure 8:
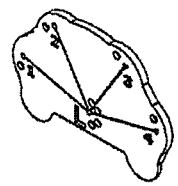
FIG. 8 is a second schematic view of the second embodiment of the tomographic reference support according to the present invention.
Figure 9:
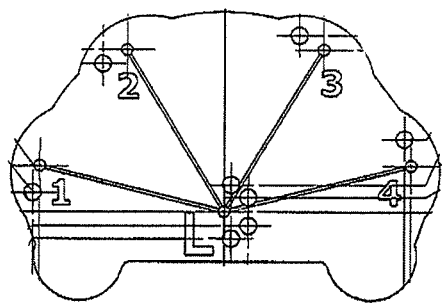
FIG. 9 is a third schematic view of the second embodiment of the tomographic reference support according to the present invention.
Figure 15:
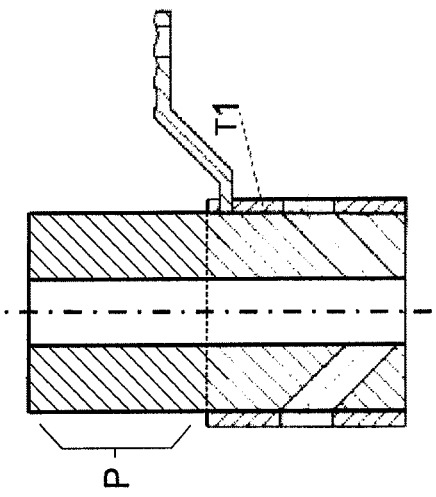
FIG. 15 is a cut side view of a second embodiment of the guide tube that is the object of the present invention, in operating position.
Figure 14:
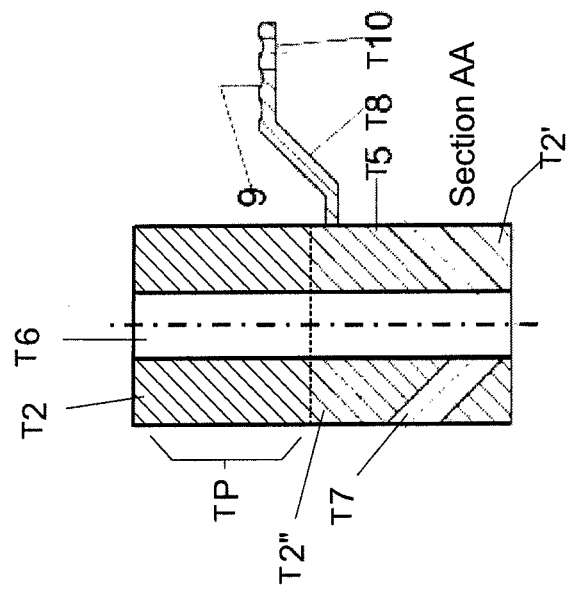
FIG. 14 is a cut side view of a second embodiment of the inner tube of the guide tube that is the object of the present invention.
Figure 17:
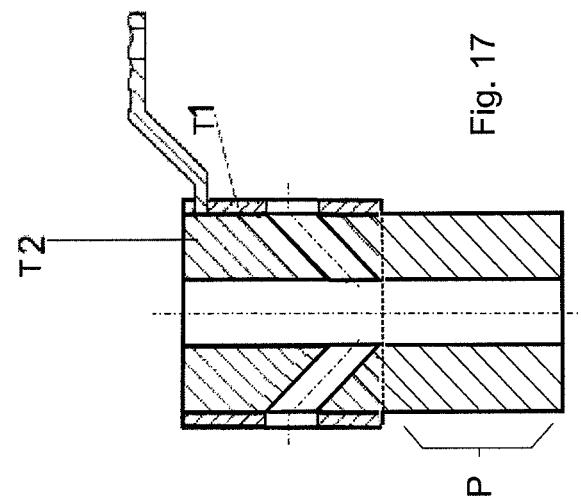
FIG. 17 is a cut side view of a third embodiment of the guide tube that is the object of the present invention, in operating position.
Figure 16:
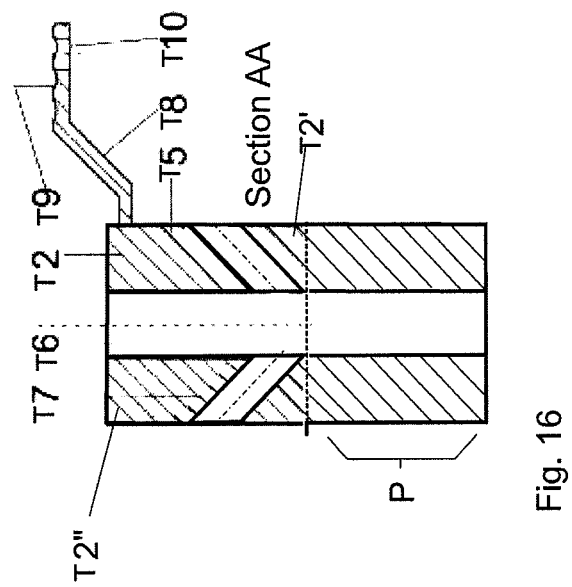
FIG. 16 is a cut side view of a third embodiment of the inner tube segment of the guide tube that is the object of the present invention.
Figure 18:
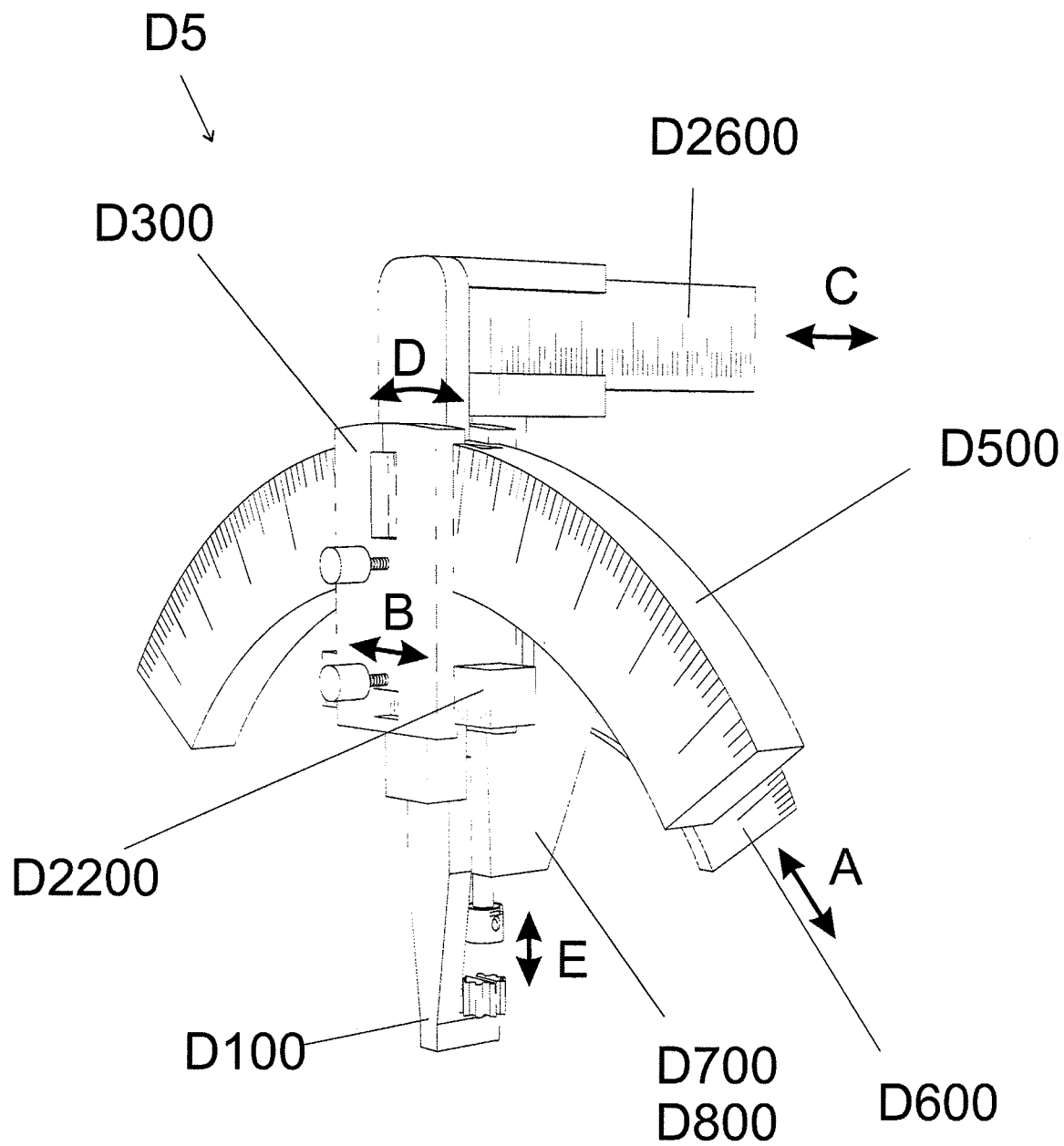
FIG. 18 is a perspective view of the guide tube positioning device that is the object of the present invention.
Figure 19:
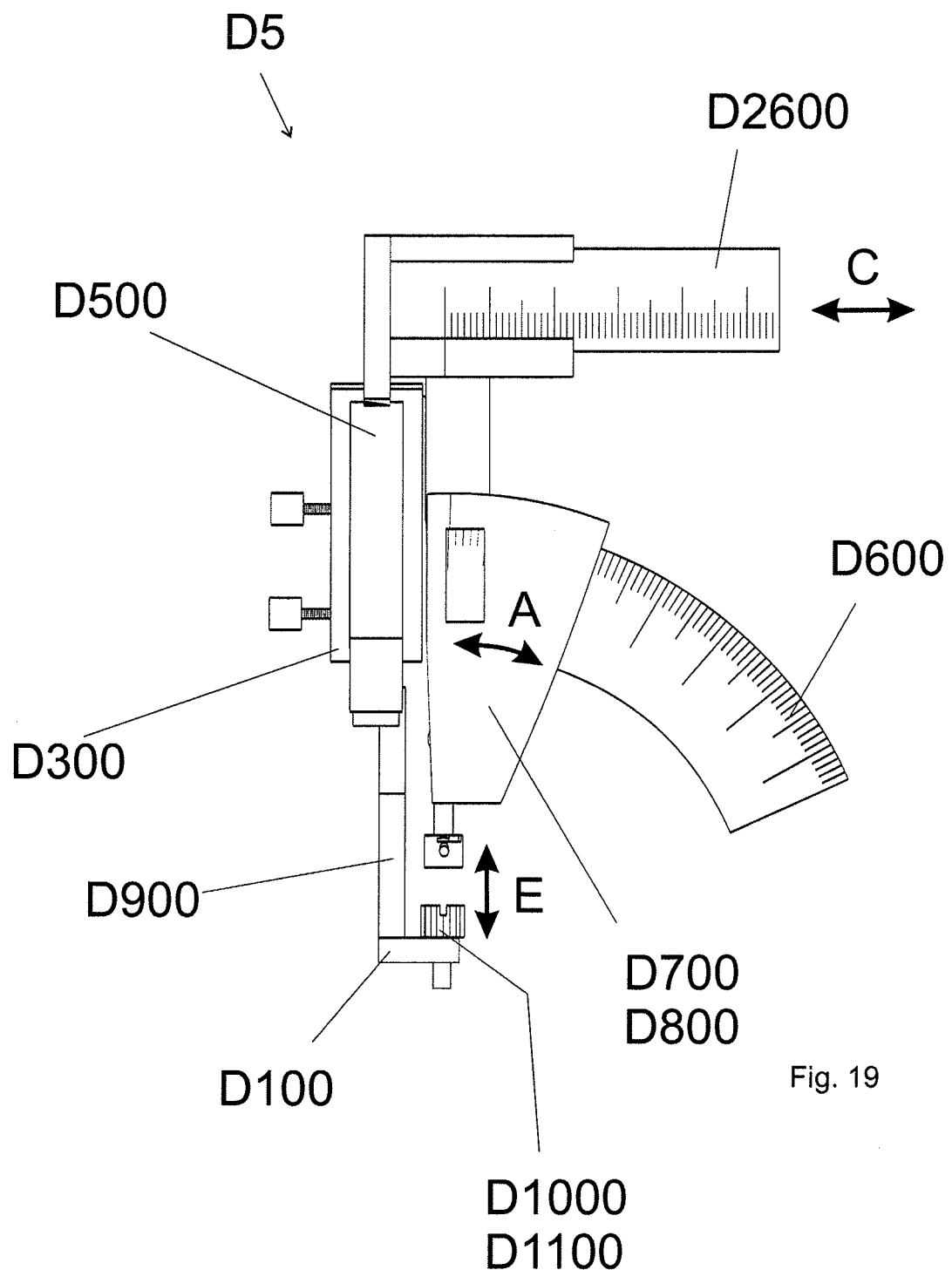
FIG. 19 is a side view of the guide tube positioning device that is the object of the present invention.
Figures 20, 21:
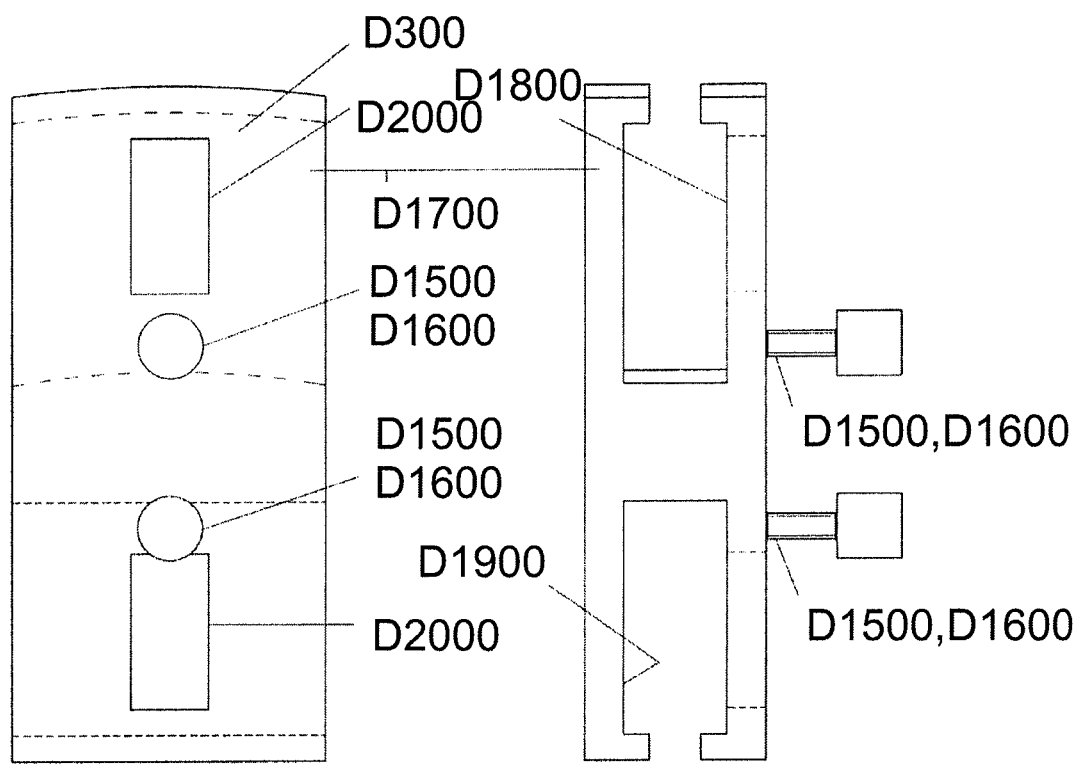
FIG. 20 is a first partial view of the guide tube positioning device that is the object of the present invention.
FIG. 21 is a second partial view of the guide tube positioning device that is the object of the present invention.
Figure 22:
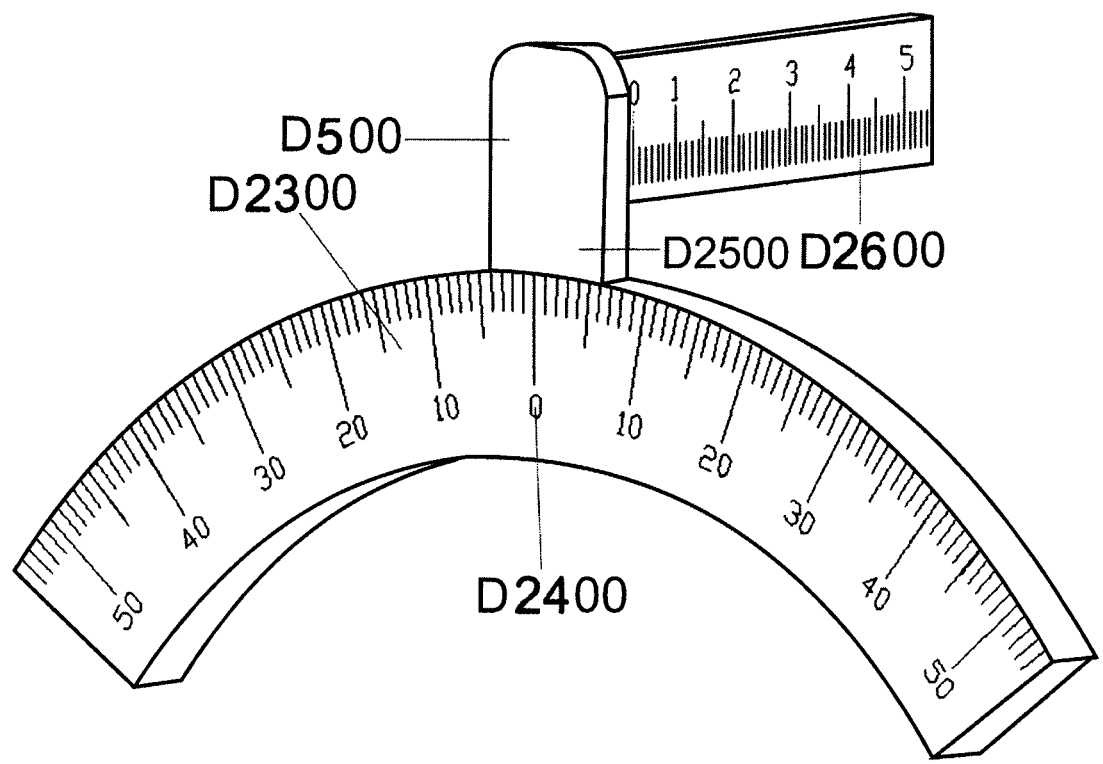
FIG. 22 is a third partial view of the guide tube positioning device that is the object of the present invention.
Figures 23, 24:
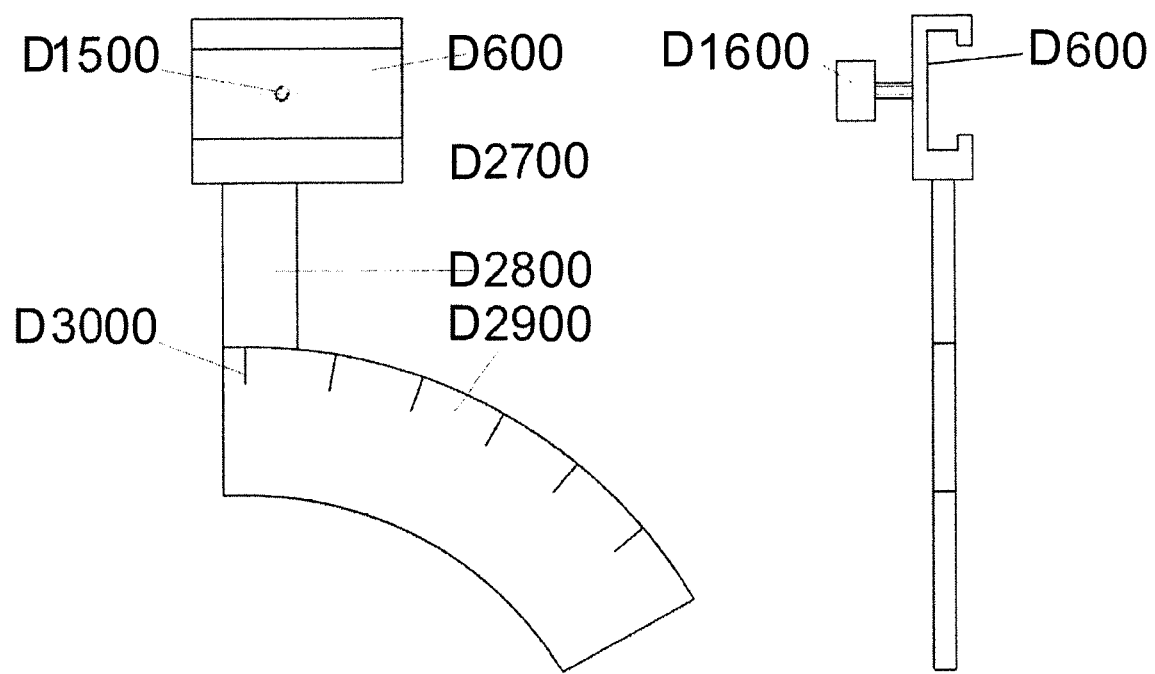
FIG. 23 is a fourth partial view of the guide tube positioning device that is the object of the present invention.
FIG. 24 is a fifth partial view of the guide tube positioning device that is the object of the present invention.
Figure 28:
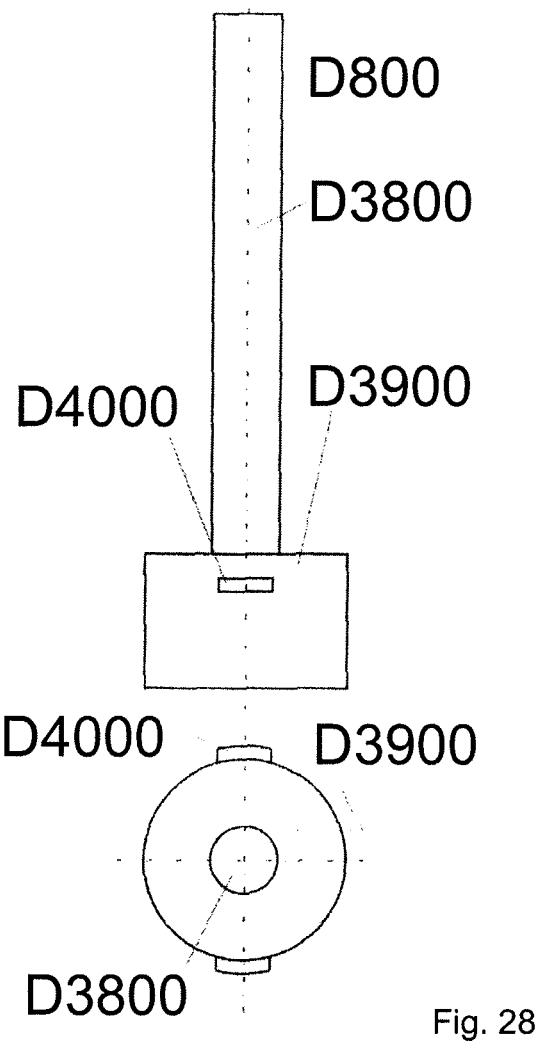
FIG. 28 is a ninth partial view of the guide tube positioning device that is the object of the present invention.
Figure 29:
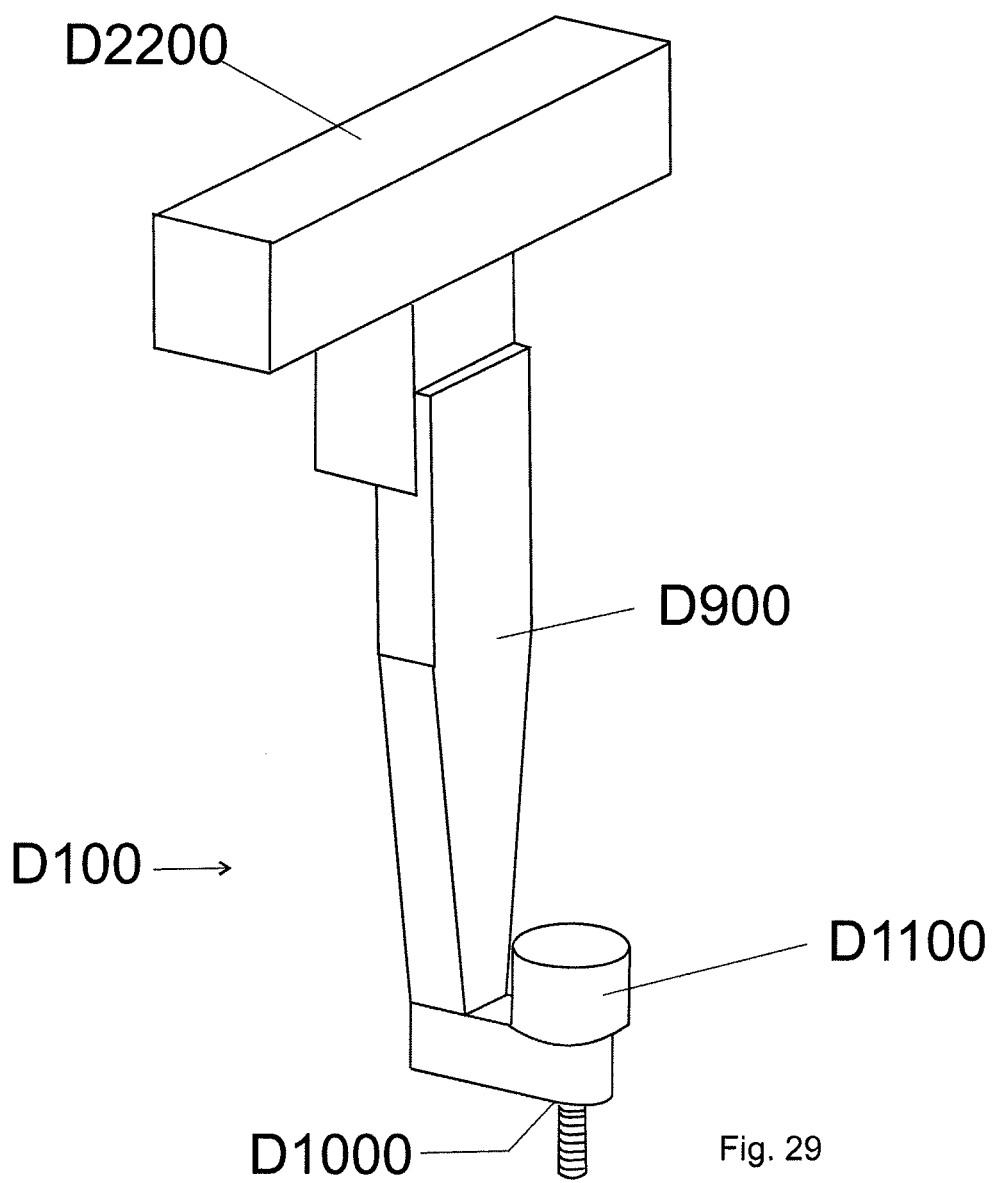
FIG. 29 is a tenth partial view of the guide tube positioning device that is the object of the present invention.

After correctly fixing the inner tube segment T2, as mentioned above (see FIG. 4), the bur or drill can be positioned inside the second axial through aperture T6. This bur, driven by a tool, then rotates and opens up an orifice in the bone tissue of the mandible or maxilla of the patient.

However, to guarantee the success of the surgery, the bone orifice must be opened up in stages, so that its diameter increases gradually. For this, the surgeon must use various inner tube segments T2, with second axial through apertures T6 having gradually larger diameters that correspond to the diameters of the bone perforation drills.

Thus, after boring the orifice with the first bur, the surgeon substitutes the inner tube segment T2 used with another one whose axial through aperture T6 is larger in diameter and, in possession of a larger-diameter bur, widens the bone orifice, and so successively, until it is finalized.

Due to the fact that the through orifices T3 and third through apertures T7 are aligned, it is possible to lubricate and refrigerate the bur positioned inside the second axial through aperture 6, or any other possible use, which is not made possible by the guide tubes from the state of the art. Said through aperture T7 links the inner part of the axial aperture T6 to the outside environment. In the absence of lubrication, the drill or bur overheats and may burn the bone tissue inside the orifice, causing subsequent necrosis. If such necrosis occurs, it will result in inflammation that will cause the loss of the implant.

The major advantage of the downwardly slanted positioning of the through apertures T7 lies in the fact that they enable the refrigeration of the tool at the final moment before it penetrates the bone, eliminating the chances of excessive heating.

Notwithstanding the benefits referred to above, the major innovation of the guide tube covered by the present invention lies in the innovative constitution of the inner tube segment T2, which comprises an integrated axial prolongation P. This prolongation has the purpose of increasing the contact surface between the drill for boring the bone and the inner aperture T6 of the inner tube T2 avoiding bending or diversion of the boring drill when drilling the orifice, particularly increasing the precision of surgery intervention.

In essence, the inner tube segment T2 comprises a first free end T2' facing the bone portion, and a second free end T2", opposite.

In a first preferred variation of the invention, the integrated axial prolongation P is projected from the second free end T2", that is, it is opposite to the bone (it therefore faces the oral cavity of the patient). In a second preferred variation, the integrated axial prolongation P is projected from the first free end T2', that is, it faces the bone. Each variation is preferred in a specific situation, to be described ahead.

In the case of the second variation, one possibility is that the integrated axial prolongation P has the same diameter as the rest of the segment and another possibility is that it has a more reduced diameter.

The existence of the integrated axial prolongation P is translated into a greater length of the inner tube segment T2, which confers greater stability of the drill or bur in its inner part, as only a small portion of the tool will be free (without being compressed by the tube) when the orifice is being bored.

When the integrated axial prolongation P is projected from the second free end T2", it faces towards the oral cavity of the patient, which is a drawback when the implant to be placed is located at the back of the mouth (pre-molar and molar regions, for example) due to the small opening of the oral cavity in this region.

However, if the implant is in the place of one of the incisors or canine teeth, this aperture limitation is rare and the axial prolongation P facing towards the mouth aperture allows, in a single-step boring, that the orifice be drilled in the bone, with millimetric precision due to the absence of diversion or bending of the tool (in most of its extension, constricted by segment T2).

To enable precise boring in the rear portion of the oral cavity, where aperture is reduced, the variation of the inner tube segment whose axial prolongation P faces the bone tissue is the most recommended.

In this situation, firstly an inner tube segment T2 without axial prolongation P is positioned inside the outer segment T1, and a first stage of partial boring is carried out. The depth of this first boring stage is reduced, in order to guarantee that only a small portion of the tool is free and that therefore there is no diversion or bending. This segment T2 does not present axial prolongation P so that it is not too high, which cannot occur in the rear region of the oral cavity due to the lack of space.

Once the first stage of partial boring is over, the segment is withdrawn and in its place another segment T2 is inserted, however, having a short length prolongation P (as a rule, the additional length of this prolongation in relation to that of the recently-withdrawn segment is equivalent to the depth of the orifice made in the first boring stage). This other segment T2 is positioned in a way that the free end of the prolongation P penetrates into the orifice partially opened up in the bone. As a result, the segment T2 is totally anchored in the bone and the diversion or bending of the drill are prevented. Also due to the penetration of the prolongation P into the orifice, the resulting height of this segment T2 in the oral cavity does not increase.

Next, the segment T2 is withdrawn and in its place another segment T2 is inserted, yet having a prolongation P of slightly longer length. This other segment T2 is positioned in a way that the free end of prolongation P penetrates into the orifice partially opened up in the bone. This segment T2 is totally anchored to the bone and drill diversion or bending is prevented, and another segment of the orifice is bored. Also due to the penetration of the prolongation P into the orifice, the height resulting from this segment T2 in the oral cavity does not increase.

Depending on the depth of the orifice to be bored, it may be necessary to substitute this segment T2 for another segment T2, whose prolongation P is of even greater length, for the performance of a fourth boring stage, as mentioned in the prior paragraphs for the second and third stages.

This boring in stages, where an inner tube segment T2 is substituted for another whose prolongation P is longer, is referred to as staggered boring or burring, and the existence of various units, each having a prolongation P of a given length, is essential for the millimetric precision obtained at the end of the orifice drilling. And, reiterating, said precision is achieved only because of the innovative constitution of the inner tube segments T2 having the prolongation P.

In short, the guide tube whose inner tube segment T2 has a prolongation P makes it feasible to increase the contact surface with the drill/bur, increasing the precision of bone burring and, consequently, the final position of the implant.

A guide tube positioning device D5 is also a new and novel invention, for it enables the positioning of the guide tube with millimetric precision on a plate which is fastened tightly and precisely on the patient's dental arch.

For the installation of the guide tube fastened to the acrylic plate, and after the tomography images have been made, the polymeric plate is withdrawn from the patient's mouth and fitted again into the plaster model. Next, the tooth and the radiopaque vertical screws are withdrawn from said plate and from the tomographic reference support, respectively, leaving only the respective orifices or protuberances, depending on the type of tomographic reference support used.

So, the guide tube positioning device D5 covered by this invention is screwed into one (or more) orifices/protuberances that received the radiopaque vertical screws, which, let it be highlighted, are vertical and are positioned in the respective tomographic support.

Since the guide tube positioning device D5 is installed on the supports S1 or S2 (exactly in the same position occupied by a radiopaque vertical screw in the case of support S1), the spatial reference on the plaster model is the same spatial reference of the tomographic examination, which made images based on the positioning of the radiopaque vertical screws.

By means of handling its components, the guide tube positioning device D5 enables the installation of the guide tube on the acrylic plate, in the exact position of the orifice which must be bored in the bone portion of the patient, regarding its positioning and vestibular-lingual and mesio-distal angles. After the correct positioning, the guide tube is fastened to the acrylic plate definitively by any joining agent, as for example, self-polymerizing acrylic resin.

Additionally, the acrylic plate is installed in the mouth of the patient and the bur/drill positioned inside the guide tube is rotated, carrying out the perforation.

The main characteristics of the guide tube positioning device D5 covered by this invention are that it is easy to manufacture, easy to operate, precise and efficient, and has a low purchase cost, to enable the accurate positioning of any guide tube already known in a polymeric plate or the like.

To facilitate the description, the guide tube positioning device will be hereinafter called 'device' D5.

A preferred embodiment of the device D5 is illustrated in the drawings and comprises at least a base D100 to which is associated at least a combination for movement D300, D500, D600, described in details further ahead. As an essential characteristic, the base D100 comprises at least a means D900, D1000, D1100 for association with the tomographic or radiographic supports.

The means for association with the definitive tomographic or radiographic support preferably comprises a fastening support D900 having a through hole D1000 e and a fastening element D1100, wherein the fastening support D900 is preferably an L-shaped bar and the fastening element D1100 is a screw having a thread, although, obviously, such specific configurations may vary. Even more preferably, the screw D1100 is housed at the front end of the bar D900.

A first horizontal graduated ruler D2200 is provided in the upper portion of the bar D900 and preferably has a thickness greater than that of the rest of the bar.

The combination for movement comprises at least a mesio-distal support D300, at least a mesio-distal goniometer and a vestibular-lingual track D500, at least a vestibular-lingual support and a vestibular-lingual goniometer D600, at least an assembler carrier 700 and at least a guide tube assembler D800.

The mesio-distal support D300 is fastened to the fastening support D900 and is comprised by a body preferably rectangular, vertical and upwardly curved D1700, having internally and transversally two through slots, a first upper slot D1800 and a second lower slot D1900. The upper slot D1800 has an upper aperture and describes the same outer curvature of the support D300, that is, its upper and lower surfaces are curves and have the same curvature radius. The lower slot 1900, in turn, has a lesser aperture.

The support D300 also comprises two open windows substantially rectangular, vertical D2000 on its forward face, having a first upper window and a second lower window. Between both windows are located two threaded holes D1500 housing screws 1600 or any other equivalently functional fastening means.

The mesio-distal goniometer support and vestibular-lingual track D500 is comprised by a graduated, circular-arched ruler D2300, the center of which D2400 is the vertical axis, and is fixed in its upper portion to a vertical support D2500 that also supports a second horizontal, graduated ruler D2600, perpendicular, in turn, to the end face of the graduated ruler D2300.

The vestibular-lingual support and vestibular-lingual goniometer D600 is comprised by a closed, horizontal U-shaped profile D2700, being open in its front portion and having a threaded hole D1500 in its rear face. Said threaded hole houses a manually-tightened screw or the like D1600.

The lower portion of the support D2700 is fastened to a vertical bar D2800 which, in turn, holds a semi-arched graduated ruler D2900, whose zero point D3000 is on the vertical plane.

The assembler carrier D700 700 is comprised by a substantially trapezoidal body D3100 whose upper face D3200 describes a curve, and having a substantially transversal inner arch-shaped slot D3300 that accompanies the curvature of the face D3200.

The carrier D700 also comprises a center-upper aperture D3400 of the slot D3300, a rectangular window D3500 on its front face D3600, two threaded orifices housing two manually-tightened screws D1600 and a substantially vertical tube D3700 embedded in its lower part.

The guide tube assembler D800 is comprised by a slender vertical axis D3800 fastened to a cylindrical base having a wider diameter D3900, which in turn has two radial and horizontal teeth D4000 that are diametrically opposite.

When the device D5 is assembled, the horizontal ruler D2200 of the base D900 is introduced into the lower slot D1900 of the support D300, fastened by the respective screw D1600.

In the upper slot D1800, the circular ruler D2300 is introduced, fastened by the respective screw D1600.

The horizontal ruler D2600 of the mesio-distal goniometer and vestibular-lingual track D500 is introduced into the profile D2700 of the vestibular-lingual support and vestibular-lingual goniometer D600.

The semicircular ruler D2900 is introduced, in turn, into the inner slot D3400 of the carrier D700.

Finally, the vertical axis D3800 of the guide tube assembler D800 é is introduced into the tube D3700 of the carrier D700, with the guide tube fitted into its free end.

After this assembly, the screw D1100 is introduced into the orifice D1000 of the base D100 and screwed in a corresponding threaded orifice provided in the tomographic supports S1 or S2. Therefore, there is no base in the literal sense of the word.

Optionally, there is also a pin or projection (not illustrated) that cooperates with said orifice S27 provided in the support S2, a fact which avoids the rotation of the device D5 over it.

To assemble the device D5 onto the supports S1 and S2, the latter must be associated with the polymeric plate, and said plate, in turn, must be positioned on top of the plaster model, as previously mentioned. Additionally, the professional must already have the information regarding the positioning of the guide tube on the plate.

In the case of the tomographic support S1 and S2, as the threaded fixing orifice was occupied by the radiopaque vertical screw used in the tomographic examination, the simple positioning of the device D5 there already guarantees its precise position, and the perpendicular line in relation to the line formed by the two radiopaque supports, based on which the tomographic examination provided the various parallel and perpendicular cuts (already commented upon previously) guarantees that this positioning does not present any error or inaccuracy. And to prevent the device D5 from rotating in relation to the orifice, the already mentioned fitting elements S103' or the orifices S27 are provided on the support.

After the physical description of the elements of the positioned device D5, a detailed explanation of its operation is provided below.

Due to constructive characteristics of the device D5, and as it can be seen in the drawings, the vestibular-lingual goniometer only manages to position the guide tube at angles above zero, counted in relation to the plane defined by the fastening support D900. For this reason, if we consider that the device D5 is positioned in one of the respective orifices that received the radiopaque vertical screws, if the vestibular-lingual positioning angle of the guide tube is negative in relation to the plane defined by the support, it will be impossible to position it. In these cases, the device D5 must be installed in another orifice of the tomographic support, to the opposite side of the dental arch, once it will operate positioned at 180 degrees and it will be possible to position the vestibular-lingual angle correctly because, operating otherwise, the vestibular-lingual angle will become positive compared to the reference (fastening support D900). A great advantage of using the support S2 in relation to the support S1 is the greater number of existing orifices, always seeking to facilitate the fastening of the device D5 and the correct positioning of the guide tube(s).

The angle is obtained from the movement of the assembler carrier D700 on the vestibular-lingual goniometer D600, illustrated in the drawings by the letter A. The angular movement can be controlled by observing the values in the scale of the vestibular-lingual goniometer D600.

Based on this, the device D5 must be handled to position the guide tube in the correct position. Considering the implant in a given tooth, from the position of the device D5 on the tomographic support (point zero), the respective elements of the movement combination must be handled for such.

In case the ideal position of the implant is deeper inside the mouth in the longitudinal sense (towards the throat), the professional moves the mesio-distal support D300 backwards (distal-wise) until the point deemed as ideal in its calculations. The movement distance can be controlled by up to one tenth of a millimeter based on the observation of values on the first horizontal ruler D2200.

In turn, if the ideal position of the implant is more outside the mouth in the longitudinal sense (towards the lips), the professional moves the mesio-distal support D300 forwards (mesial-wise) until the point deemed ideal in his calculations.

The mesio-distal movement can be seen in the drawings by the letter B.

Having defined the ideal position of the guide tube in the longitudinal sense, the professional now positions it transversally (towards the tongue—lingual—or towards the checks—vestibular).

As already mentioned, the positioning of the device D5 may vary according to the vestibular-lingual angle under which the guide tube must be positioned.

In view of the positioning of the device D5, the vestibular-lingual support and vestibular-lingual goniometer D600 is moved slightly vestibular-wise or lingual-wise until the ideal transversal position is found. This movement is illustrated in the drawings by the letter C. The movement can be controlled by observing the values on the scale of the second horizontal graduated ruler D2600.

After the mesio-distal position, the vestibular-lingual angle and the vestibular-lingual position were marked, all that remains is to correctly position the tube in relation to the mesio-distal angle, which can be made by moving the vestibular-lingual support and vestibular-lingual goniometer D600 in relation to the mesio-distal goniometer D500. As the track is curved, such movement generates an angular mesio-distal rotation of the goniometer D500. The angular movement can be controlled by observing the values on the scale of the mesio-distal goniometer D500 and is represented in the drawings by letter D.

Please note that the device D5 is constituted with such a geometry that the radius center of both goniometers is precisely the point where it is fastened to the tomographic supports S1 or S2.

Finally, the guide tube assembler D800 is lowered until it is positioned at the level of the acrylic plate, to which it is fastened. This movement is represented in drawings with the letter E. Next, the assembler D800 is hoisted and the guide tube remains fastened to the plate.

Also preferably, each kind of linear (mesial, distal, vestibular and lingual) or angular (mesial, distal, vestibular and lingual) movement is easily identified with the application of colors to the respective numeric scales, which significantly facilitates the identification of the movement to be performed by those not very skilled in the art.

The device D5 has numerous advantages, including simplicity of manufacture and operation, precision, efficiency, low purchase cost, lightness, portability, lack of periodic maintenance, no need for very specialized manpower for handling and the equipment is able to position the outer guide tube both with information obtained from a tomography and with information obtained from a radiography associated with gingival sounding.

Due to its small size, the amplitude of movements for having the guide tube correctly positioned is small, making it more accurate in operation.

However, obviously the constitution of the device D5 may vary without having it excluded from the protection scope of the invention. It is sufficient that it comprises at least one element for movement seeking the correct determination for the positioning of the first outer tube segment.

Figure 30:
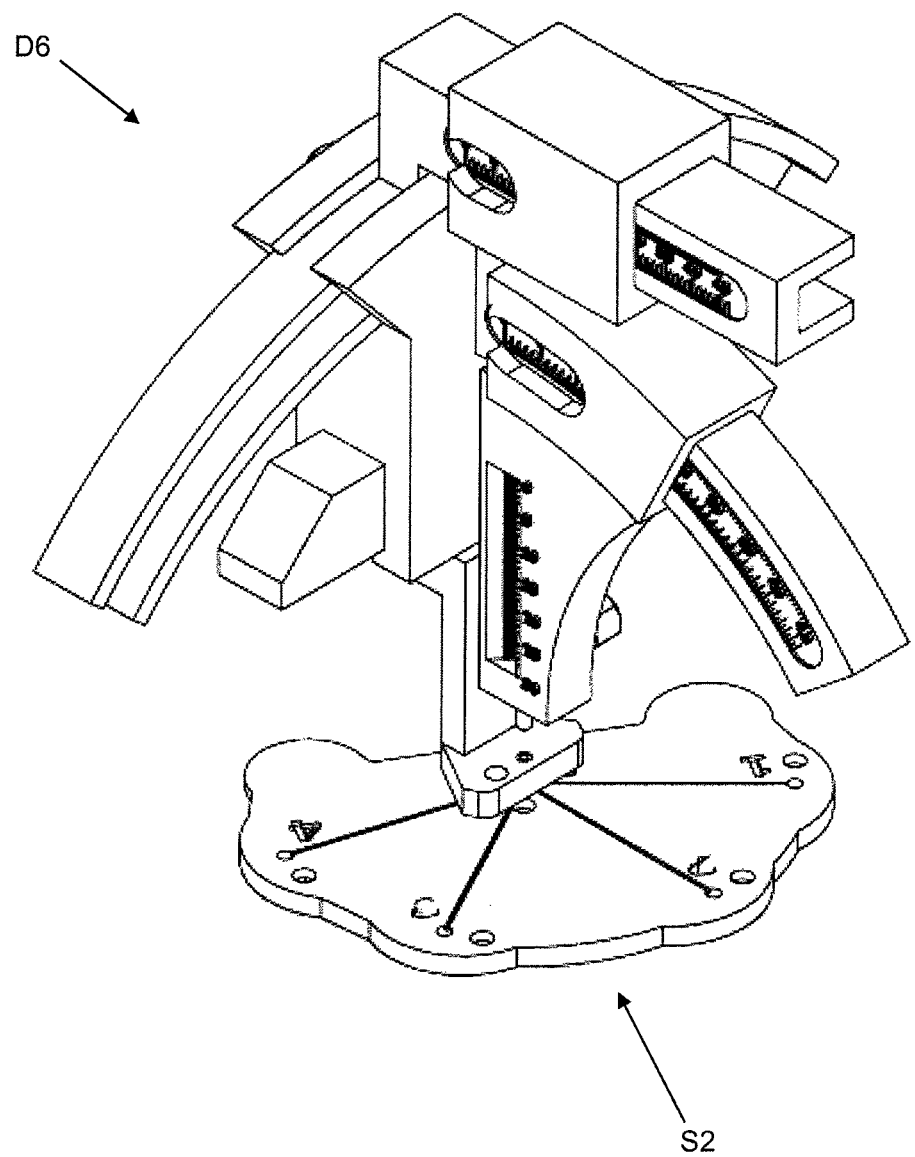
FIG. 30 is a perspective view of the guide tube positioning device connected to the second embodiment of the tomographic reference support according to the present invention.
Figure 31:
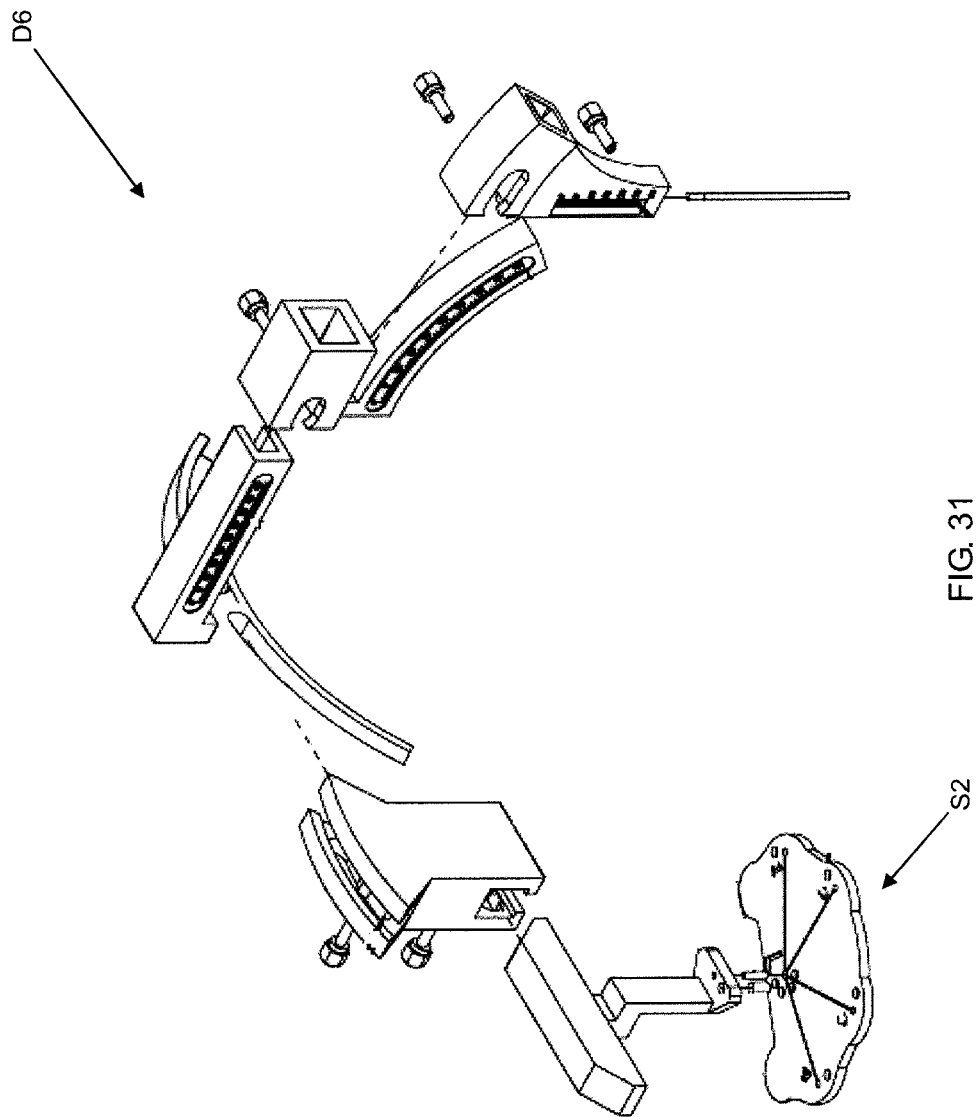
FIG. 31 is a schematic view of the guide tube positioning device connected to the second embodiment of the tomographic reference support according to the present invention.

Alternatively, other embodiments of the device D5 can be provided, such as one having an integrated base, where the plaster mold is positioned on this base, and the equipment is calibrated so that the zero position is where the orifice is located for the positioning of the radiopaque vertical screw. In a preferred embodiment, as shown in FIGS. 30 and 31, the guide tube positioning device D6 has a scale of vertical movement which determines the depth in relation to the referential plane in which the guide tube is fixed.

Other more elaborate alternatives comprise a digital computer-controlled device, electrically moveable by means of stepping motors, in which the operator merely feeds the coordinates into the computer and all movements mentioned above for the correct positioning of the guide tube are made electrically.

Having described the constructive features of the present invention, the steps of a preferential embodiment of the method for positioning a guide tube on a plate/template for installation of an implant will be provided below:

Step A—Creating a model of the patient's dental arch;

Step B—Positioning a synthetic prosthetic crown in the place of a missing tooth (which may have been originally missing in the patient's mouth, or may correspond to a tooth to be extracted and replaced by a prosthetic crown, in which case the professional removes the tooth from the model before positioning the prosthetic crown) in the model of the patient's dental arch;

Step C—Creating a plate of polymeric material based on the model of the dental arch associated with the synthetic prosthetic crown;

Step D—Fastening, with a radiolucent joining agent, the tomographic support S2 associated with the radiopaque screws S25, to the molded plate of polymeric material coupled to the model of the dental arch;

Step E—Decoupling, from the model of the dental arch, the plate of polymeric material fastened to the tomographic support S2, and removing the synthetic prosthetic crown positioned in the place of the missing tooth;

Step F—Filling, in the plate of polymeric material fastened to the tomographic support S2, the place of the missing tooth with a radiopaque prosthetic crown for carrying out the tomographic examination(s);

Step G—Fitting, over the patient's dental arch, the plate of polymeric material filled in with the radiopaque prosthetic crown and fastened to the tomographic support S2, and tomographically scanning the patient's face;

Step H—Using the computer program to determine the ideal positioning of the orifice and installation of the guide tube;

Step I—Removing the radiopaque prosthetic crown from the plate of polymeric material fastened to the tomographic support S2 and drilling an orifice in the plate for the positioning of the guide tube;

Step J—Removing the radiopaque screws S25 from the tomographic support S2 fastened to the plate of polymeric material and screwing the guide tube positioning device (D5 or D6), configured according to the information from the computer program, at the same position occupied by one of the radiopaque screws S25;

Step L—Positioning the guide tube in the orifice drilled in the plate of polymeric material fastened to the tomographic support S2 and definitively fastening the guide tube with a radiolucent joining agent; and Step M—Removing the guide tube positioning device from the plate of polymeric material fastened to the tomographic support S2 and fitting the support S2 into the patient's dental arch.

Finally, any configuration can be proposed as long as it is functional.

Having described examples of preferred embodiments, it should be understood that the scope of the present invention encompasses other possible variations, and is limited only by the content of the attached claims, other possible equivalents being included therein.

What is claimed is:

1. A guide tube positioning device for positioning a guide tube on a polymeric plate, the guide tube being adapted for guiding a drill or bur used for boring an orifice in a dental patient's bone for receiving an implant that will support a prosthetic crown, the polymeric plate being configured to be fitted over the patient's dental arch to be used as a template, the guide tube positioning device comprising:

a base on which at least a movement mechanism is mounted, wherein the base comprises at least one means for affixing a radiographic or tomographic support on the base, wherein the movement mechanism comprises a mesio-distal support defining a mesio-distal track that has a curved circular arch shape extending along a mesio-distal direction, and a mesio-distal goniometer slidable within the mesio-distal track, the mesio-distal goniometer comprising a graduated ruler having a curved circular arch shape along the mesio-distal direction, wherein the movement mechanism further comprises an assembler carrier having a guide tube assembler depending therefrom, the guide tube assembler defining a lower free end that is configured for receiving and holding the guide tube to be positioned on the polymeric plate, the assembler carrier defining a vestibular-lingual track that has a curved circular arch shape extending along a vestibular-lingual direction, and further comprises a vestibular-lingual goniometer slidable within the vestibular-lingual track, the vestibular-lingual goniometer comprising a graduated ruler having a curved circular arch shape along the vestibular-lingual direction, and wherein the vestibular-lingual goniometer is supported on the mesio-distal goniometer, the movement mechanism thereby effecting vestibular-lingual adjustment of the guide tube assembler by movement of the assembler carrier along the vestibular-lingual goniometer, and effecting mesio-distal adjustment of the guide tube assembler by movement of the mesio-distal support along the mesio-distal goniometer.

2. The guide tube positioning device according to claim 1, wherein the means for affixing the radiographic or tomographic support comprises a fixing support having a through hole and a fixing element.

3. The guide tube positioning device according to claim 2, wherein the fixing support is an L-shaped bar and the fixing element is a screw having a thread.

4. A guide tube positioning and support assembly to enable the correct positioning of a guide tube on a plate to be used as a template on a patient's dental arch, comprising:

a plurality of radiopaque reference elements;

a radiographic or tomographic support comprising a body defining a plurality of fixing orifices therein for respectively receiving the radiopaque reference elements in removable fashion; and a guide tube positioning device comprising a base and a movement mechanism supported on the base, wherein the base comprises a fixing element engageable with a selected one of the fixing orifices in the radiographic or tomographic support, after the radiopaque reference element has been removed therefrom, for fixing the guide tube positioning device on the radiographic or tomographic support, wherein the movement mechanism comprises a mesio-distal support defining a mesio-distal track that has a curved circular arch shape extending along a mesio-distal direction, and a mesio-distal goniometer slidable within the mesio-distal track, the mesio-distal goniometer comprising a graduated ruler having a curved circular arch shape along the mesio-distal direction, wherein the movement mechanism further comprises an assembler carrier having a guide tube assembler depending therefrom, the guide tube assembler defining a lower free end that is configured for receiving and holding the guide tube to be positioned on the plate, the assembler carrier defining a vestibular-lingual track that has a curved circular arch shape extending along a vestibular-lingual direction, and further comprises a vestibular-lingual goniometer slidable within the vestibular-lingual track, the vestibular-lingual goniometer comprising a graduated ruler having a curved circular arch shape along the vestibular-lingual direction, and wherein the vestibular-lingual goniometer is supported on the mesio-distal goniometer, the movement mechanism thereby effecting vestibular-lingual adjustment of the guide tube assembler by movement of the assembler carrier along the vestibular-lingual goniometer, and effecting mesio-distal adjustment of the guide tube assembler by movement of the mesio-distal support along the mesio-distal goniometer.

5. The guide tube positioning and support assembly according to claim 4, wherein the guide tube positioning device comprises a fixing support having a through hole for the fixing element.

6. The guide tube positioning and support assembly according to claim 5, wherein the fixing support is an L-shaped bar and the fixing element is a screw having a thread.

* * * * *